US009488822B2

(12) United States Patent
Machida et al.

(10) Patent No.: US 9,488,822 B2
(45) Date of Patent: Nov. 8, 2016

(54) SLIDE TRAY AND SLIDE CONVEYOR APPARATUS

(71) Applicant: Sony Corporation, Tokyo (JP)

(72) Inventors: Yuuichi Machida, Kanagawa (JP); Yu Hirono, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 14/419,799

(22) PCT Filed: Aug. 6, 2013

(86) PCT No.: PCT/JP2013/004743
§ 371 (c)(1),
(2) Date: Feb. 5, 2015

(87) PCT Pub. No.: WO2014/027450
PCT Pub. Date: Feb. 20, 2014

(65) Prior Publication Data
US 2015/0205089 A1 Jul. 23, 2015

(30) Foreign Application Priority Data
Aug. 13, 2012 (JP) ................... 2012-179581

(51) Int. Cl.
G02B 21/26 (2006.01)
G02B 21/34 (2006.01)
G01N 1/31 (2006.01) G02B 21/24 (2006.01)
B01L 9/00 (2006.01)

(52) U.S. Cl.
CPC .............. G02B 21/34 (2013.01); B01L 9/52 (2013.01); G01N 1/312 (2013.01); G02B 21/24 (2013.01); B01L 2200/025 (2013.01); B01L 2300/0822 (2013.01); G02B 21/26 (2013.01)

(58) Field of Classification Search
CPC .............. G01N 1/312; G01N 2035/00138; G01N 2201/0446; G02B 21/16; G02B 21/26; G02B 21/34; G02B 21/362
USPC ................ 359/391, 368, 388, 398, 396
See application file for complete search history.

(56) References Cited

U.S. PATENT DOCUMENTS

2010/0135861 A1* 6/2010 Sage ............... G02B 21/34
422/400
2012/0075695 A1 3/2012 Deblasis et al.

FOREIGN PATENT DOCUMENTS

| JP | 07-291386 | 11/1995 |
| JP | 10-273184 | 10/1998 |
| JP | 2004-262465 | 9/2004 |

OTHER PUBLICATIONS

International Search Report issued in connection with International Patent Application No. PCT/JP2013/004743, dated Nov. 5, 2013. (2 pages).

Primary Examiner — Euncha Cherry
(74) Attorney, Agent, or Firm — Chip Law Group

(57) ABSTRACT

To provide a slide tray having excellent practicality, convenience, operability, and the like, and a conveyor apparatus that conveys slides accommodated in the slide tray. A slide tray according to an embodiment of the present disclosure includes a slide accommodation portion capable of accommodating one or more slides mounted thereon, and a switch portion that makes a switch between a first state in which an entire surface of the one or more slides is mounted on the slide accommodation portion and a second state in which one end portion of the one or more slides is released from the slide accommodation portion.

12 Claims, 24 Drawing Sheets

SLIDE TRAY AND SLIDE CONVEYOR APPARATUS

CROSS REFERENCES TO RELATED APPLICATIONS

The present application is a national stage of International Application No. PCT/JP2013/004743 filed on Aug. 6, 2013 and claims priority to Japanese Patent Application No. 2012-179581 filed on Aug. 13, 2012, the disclosure of which is incorporated herein by reference.

BACKGROUND

Technical Field

The present disclosure relates to a slide tray that accommodates slides and a slide conveyor apparatus that conveys slides accommodated in the slide tray.

In the fields of medical care, pathologies, and the like, a slide tray that accommodates a plurality of orderly-arranged light microscope slide glasses (hereinafter, simply referred to as "slides") onto which sections of biological cells, tissues, organs, and the like are mounted is widely known (see, for example, Patent Document 1). In general, on such a slide tray, four sides of a slide as a rectangular thin plate are surrounded by partitions for sectioning the slide from adjacent slides. Although it is necessary to take out the slide from the slide tray for observing the slide with the light microscope, since the slide is surrounded by the partitions, it is difficult to take out the slide from the slide tray. On the other hand, there is known a scanner apparatus that scans and digitizes a plurality of slides. In scanning the slides using the scanner apparatus, it is general to manually move the plurality of slides accommodated in the slide tray into a cassette dedicated for the scanner apparatus. Considering the problem that it is difficult to take out the slide from the slide tray, manually moving the plurality of slides one by one is a laborious task. As described above, there is still room for improvement regarding practicality, convenience, operability, and the like of the slide tray.

Patent Document 1: Japanese Patent Application Laid-open No. Hei 07-291386

SUMMARY

Problem to be Solved by the Invention

In view of the circumstances as described above, it is an object of the present disclosure to provide a slide tray having excellent practicality, convenience, operability, and the like. It is another object of the present disclosure to provide a conveyor apparatus that conveys slides accommodated in the slide tray.

Means for Solving the Problem

According to an embodiment of the present disclosure, there is provided a slide tray including: a slide accommodation portion capable of accommodating one or more slides mounted thereon; and a switch portion that makes a switch between a first state in which an entire surface of the one or more slides is mounted on the slide accommodation portion and a second state in which one end portion of the one or more slides is released from the slide accommodation portion.

A mount position of the one or more slides in the second state is tilted a predetermined angle with respect to a mount position of the one or more slides in the first state.

The slide accommodation portion includes a first accommodation portion that accommodates the one end portion of the one or more slides, and a second accommodation portion that accommodates a part of the one or more slides excluding the one end portion, the second accommodation portion being spatially apart from the first accommodation portion. The switch portion makes a switch from the first state to the second state by tilting the second accommodation portion.

The switch portion makes a switch from the first state to the second state by tilting the second accommodation portion using one end portion of the second accommodation portion distant from the first accommodation portion as a fulcrum.

The switch portion tilts the second accommodation portion using the one end portion of the second accommodation portion as a fulcrum by lifting the second accommodation portion from below.

The slide tray further includes a frame that accommodates the slide accommodation portion, and a first support portion that rotatably supports the one end portion of the second accommodation portion with respect to the frame. The switch portion makes a switch from the first state to the second state by tilting the second accommodation portion using the first support portion as a fulcrum.

The slide tray further includes: a connection portion that relatively and bendably connects the first accommodation portion and the second accommodation portion; and a second support portion that rotatably supports one end portion of the first accommodation portion distant from the second accommodation portion with respect to the frame and supports the one end portion of the first accommodation portion such that the one end portion is movable in a direction in which the first accommodation portion and the second accommodation portion are adjacent to each other. The switch portion makes a switch from the first state to the second state by tilting the second accommodation portion using the first support portion as a fulcrum and moving the one end portion of the first accommodation portion in an approaching direction with respect to the second accommodation portion.

According to an embodiment of the present disclosure, there is provided a slide conveyor apparatus including: a switch portion that switches a slide accommodation portion of a slide tray, which is capable of accommodating one or more slides mounted thereon, between a first state in which an entire surface of the one or more slides is mounted on the slide accommodation portion and a second state in which one end portion of the one or more slides is released from the slide accommodation portion; a grip portion that grips the one end portion of the slide accommodated in the slide accommodation portion switched to the second state; and a conveyor portion that conveys the slide gripped by the grip portion by moving the grip portion.

A mount position of the one or more slides in the second state is tilted a predetermined angle with respect to a mount position of the one or more slides in the first state.

The slide accommodation portion includes a first accommodation portion that accommodates the one end portion of the one or more slides, and a second accommodation portion that accommodates a part of the one or more slides excluding the one end portion, the second accommodation portion being spatially apart from the first accommodation portion. The switch portion makes a switch from the first state to the second state by tilting the second accommodation portion.

The switch portion makes a switch from the first state to the second state by tilting the second accommodation portion using one end portion of the second accommodation portion distant from the first accommodation portion as a fulcrum.

The switch portion tilts the second accommodation portion using the one end portion of the second accommodation portion as a fulcrum by lifting the second accommodation portion from below.

Effect of the Invention

According to the present disclosure, it is possible to provide a slide tray having excellent practicality, convenience, operability, and the like, and a conveyor apparatus that conveys slides accommodated in the slide tray.

Additional features and advantages are described herein, and will be apparent from the following Detailed Description and the figures.

DETAILED DESCRIPTION

Hereinafter, an embodiment of the present disclosure will be described with reference to the drawings.

Embodiment

1. Outline of Slide Tray

In general, on a slide tray, four sides of a slide as a rectangular thin plate are surrounded by partitions for sectioning the slide from a plurality of adjacent slides. To take out a slide from such a slide tray, it is general to stick a finger into a gap between the partition and the slide, lift the slide, and pinch the slide and take it out. It is desirable for the accommodation sections of the slide tray to be larger than the size of the slides for securing the gap to insert the finger. However, since a large number of (e.g., several ten) slides are to be accommodated in a single slide tray, the overall slide tray will become large if the accommodation sections of all slides are to be secured. On the other hand, if the accommodation sections of the slide tray are set such that the four sides of each slide come into contact with the partitions, it becomes difficult to take out the slides despite the fact that the problem of the slide tray becoming large will be solved.

In view of the circumstances as described above, it is an object of the present disclosure to provide a slide tray that enables slides to be easily taken out from the slide tray by hand without enlarging the overall slide tray.

2. Structure of Slide Tray

Figure 1:
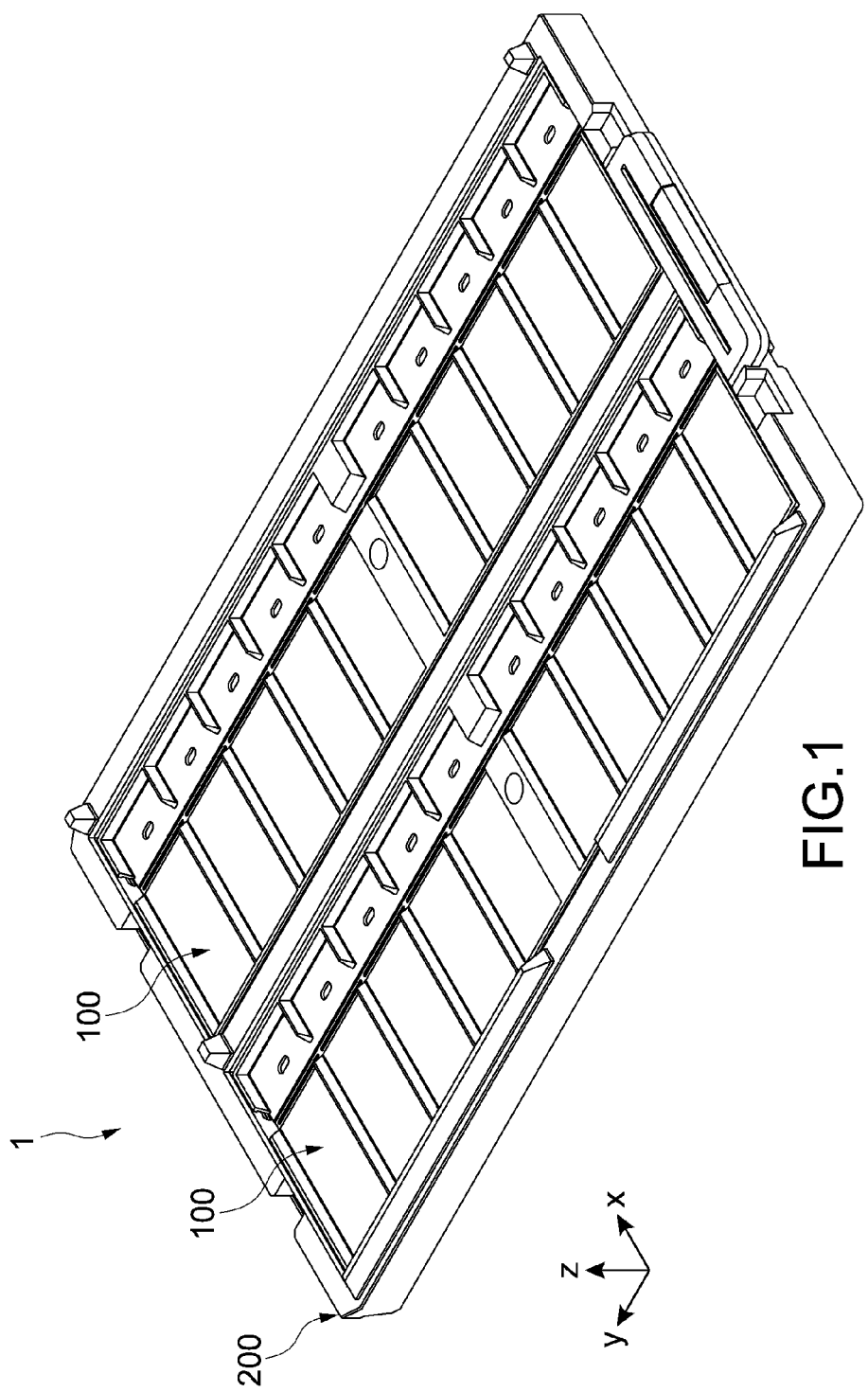
FIG. 1 is a perspective view of a slide tray according to an embodiment of the present disclosure.
Figure 2:
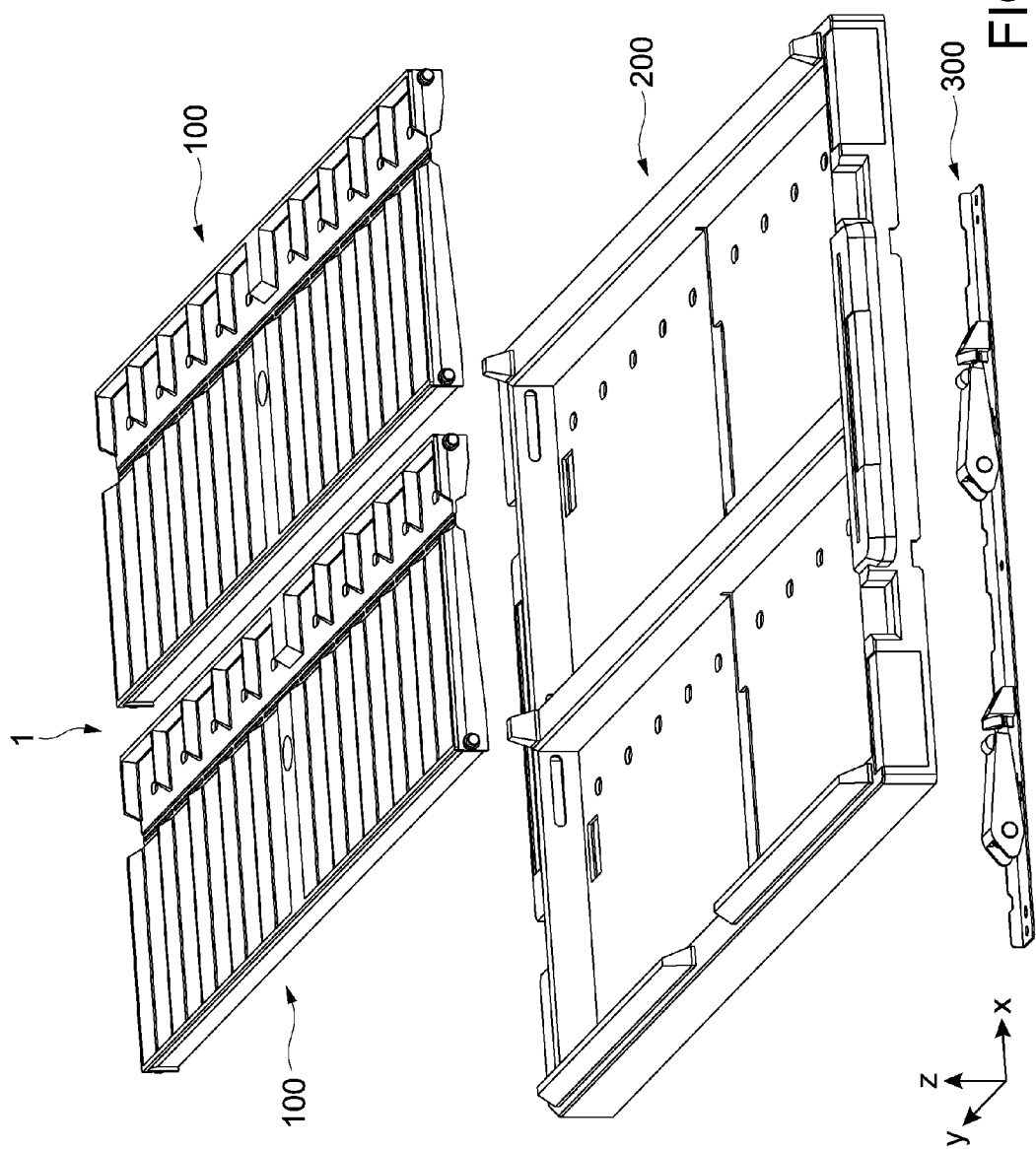
FIG. 2 is an exploded perspective view of the slide tray according to the embodiment.

FIG. 1 is a perspective view of a slide tray 1 according to this embodiment. FIG. 2 is an exploded perspective view of the slide tray 1 of this embodiment.

The slide tray 1 includes one or more slide accommodation portions 100, a frame 200, and a flip-up portion 300 (see FIG. 2, switch portion).

The one or more slide accommodation portions 100 are each capable of accommodating a plurality of slides mounted thereon. While being accommodated in the slide accommodation portions 100, entire surfaces of the plurality of slides are mounted on the slide accommodation portions 100 (non-tilted state, first state).

The frame 200 is a rectangular frame in which one or more slide accommodation portions 100 are set.

Figure 3:
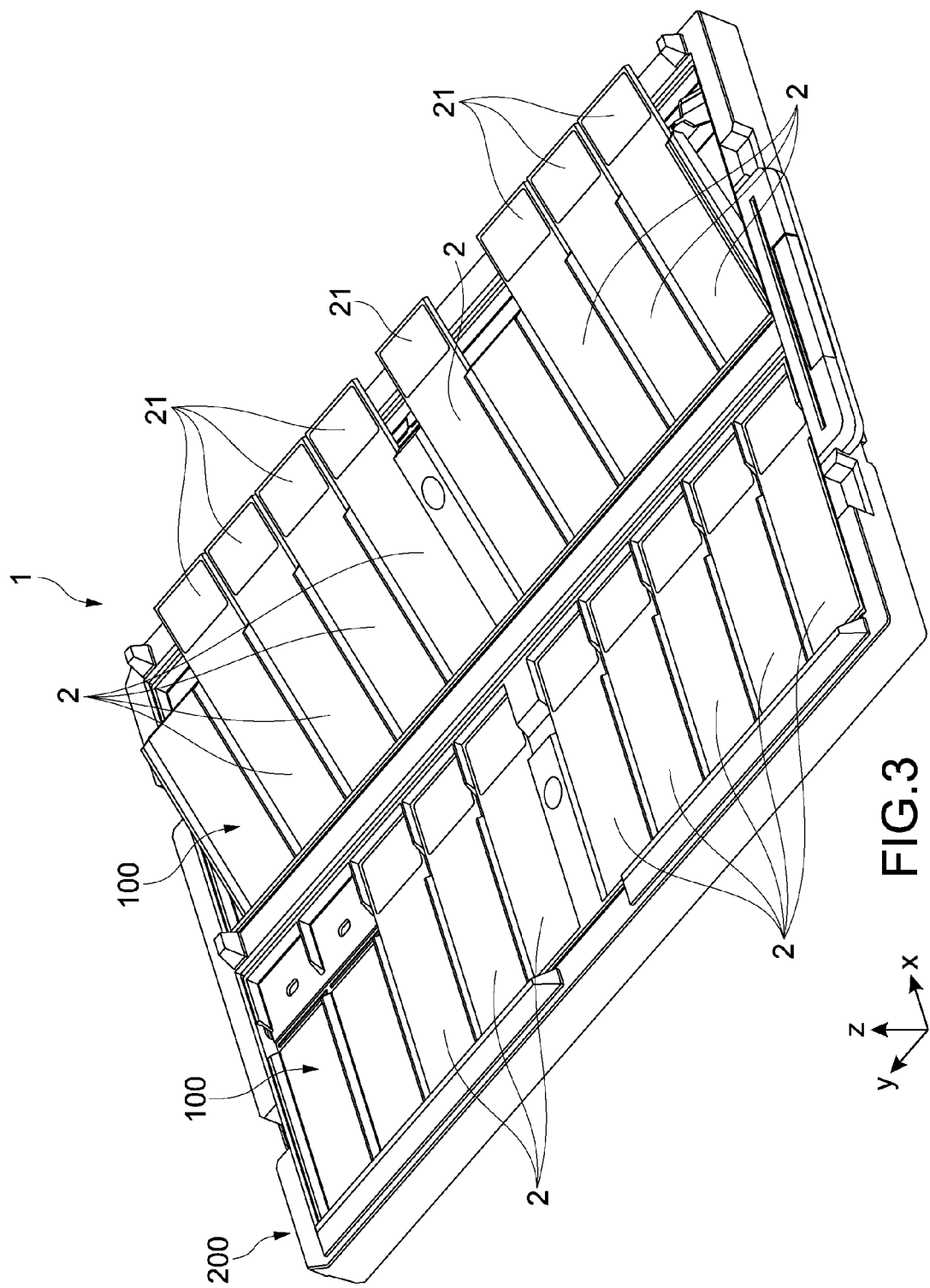
FIG. 3 is another perspective view of the slide tray according to the embodiment showing a state different from that shown in FIG. 1 in which a plurality of slides are accommodated in the slide tray.

FIG. 3 is another perspective view of the slide tray 1 according to this embodiment showing a state different from that shown in FIG. 1 in which a plurality of slides 2 are accommodated in the slide tray 1.

The flip-up portion 300 (see FIG. 2) is provided in the frame 200. The flip-up portion 300 is switched between a non-tilted state (see FIG. 1) where the slide accommodation portions 100 are flat (non-tilted) with respect to the frame 200 and a tilted state (see FIG. 3) where the slide accommodation portions 100 are tilted with respect to the frame 200. A mount position of the slides 2 in the tilted state (second state) is tilted a predetermined angle with respect to that of the slides 2 in the non-tilted state (first state). In the tilted state (second state), one end portion 21 of the slide 2 is released from the slide accommodation portion 100. Hereinafter, structures of the one or more slide accommodation portions 100, the frame 200, and the flip-up portion 300 will be described in detail.

It should be noted that in the specification, the term "rectangle" not only refers to an exact rectangle (i.e., square in which four corners are right angles and two opposing sides have the same length) but also to a practically rectangular shape. For example, even when an angle formed by two orthogonal sides is round or notched, the shape is referred to as "rectangle". Moreover, even when an arbitrary side has irregularities, the shape is referred to as "rectangle" as long as it has a rectangular impression as a whole.

2.1. Structure of Slide Accommodation Portion

Figure 4:
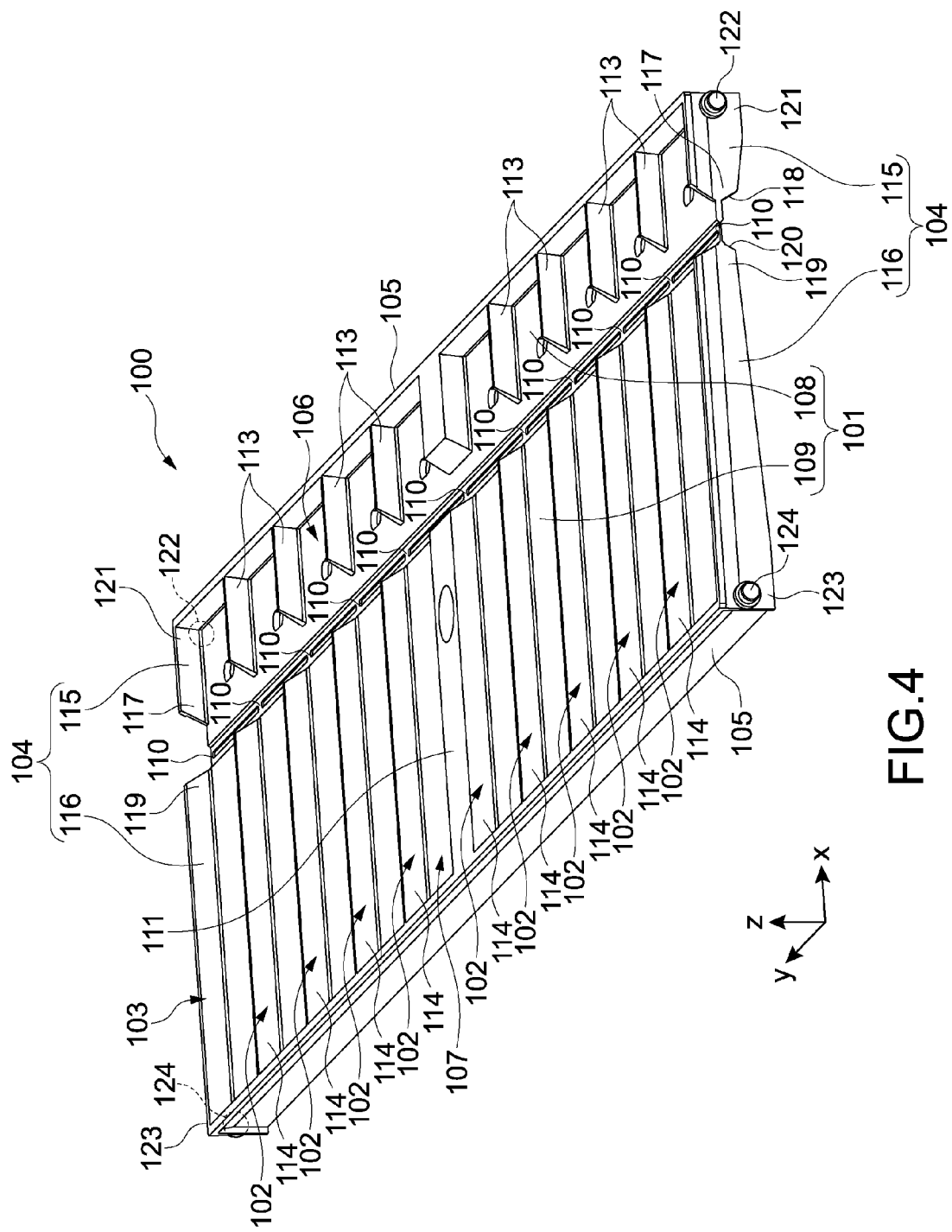
FIG. 4 is a perspective view of a slide accommodation portion.

FIG. 4 is a perspective view of the slide accommodation portion.

The one or more slide accommodation portions 100 have the same structure. Therefore, in the descriptions below, unless there is a need to distinguish the slide accommodation portions 100 from one another, the slide accommodation portions 100 will be referred to as "slide accommodation portion 100", and descriptions will be given on a single slide accommodation portion 100.

The slide accommodation portion 100 includes a mount plate 101, a plurality of partitions 102, and an outer frame 103. On the mount plate 101, a plurality of slides can be mounted adjacently.

The plurality of partitions 102 each protrude from the mount plate 101 in a direction orthogonal to the mount plate 101 to thus section the mount plate 101 on which the plurality of slides (slides 2 in FIG. 3) are mounted adjacently. As a result, the plurality of slides are separated from one another. Specifically, the plurality of partitions 102 section the mount plate 101 such that the plurality of slides can be arranged in parallel in one line while long sides of the plurality of slides as rectangular thin plates are adjacent to each other and one surface of the slides is entirely mounted on the mount plate 101. The plurality of partitions 102 restrict longitudinal movements of the slides mounted on the mount plate 101.

It should be noted that in the descriptions hereinafter, a longitudinal direction of the plurality of slides (short side direction of slide) on the mount plate 101 is referred to as Y direction, a direction orthogonal to the Y direction (long side direction of slide) on the mount plate 101 is referred to as X direction, and a direction orthogonal to the mount plate 101 (thickness direction of slide) is referred to as Z direction.

The outer frame 103 surrounds the circumference of the mount plate 101 and protrudes from the mount plate 101 in the Z direction. A Z-direction height of the outer frame 103 from the mount plate 101 and that of the plurality of partitions 102 from the mount plate 101 are the same. More specifically, the Z-direction heights of the outer frame 103 and the plurality of partitions 102 are set to be larger than a thickness of a general slide. The outer frame 103 includes a pair of first outer frames 104 extending in the X direction and a pair of second outer frames 105 extending in the Y direction. The pair of first outer frames 104 restrict Y-direction movements of the slides positioned at both ends in the longitudinal direction. The pair of second outer frames 105 restrict X-direction movements of the plurality of slides. As described above, the slides are arranged such that four sides thereof come into contact with the outer frame 103 and the partitions 102 as a partition portion. In this state, the outer frame 103 and the partitions 102 as the partition portion restrict movements of the slides.

The structure of the slide accommodation portion 100 will be described in more detail. The slide accommodation portion 100 includes a first accommodation portion 106 and a second accommodation portion 107. The length of the first accommodation portion 106 in the X direction is smaller than that of the second accommodation portion 107 in the X direction. Specifically, the first accommodation portion 106 accommodates one end portion of the plurality of slides (one end portion 21 of the slide 2 in FIG. 3). For example, one end portion of the slide is an end portion of the slide in the long side direction (X direction) where there is generally no notch or the like and is a part corresponding to an area where a label is to be attached. The second accommodation portion 107 accommodates a part of the plurality of slides excluding the one end portion. The first accommodation portion 106 and the second accommodation portion 107 are continuous in the X direction but are spatially separated. Hereinafter, the structures of the first accommodation portion 106 and the second accommodation portion 107 will be described in more detail.

The mount plate 101 includes a first mount plate 108 provided in the first accommodation portion 106 and a second mount plate 109 provided in the second accommodation portion 107. On the first mount plate 108, the one end portion of the plurality of slides is mounted. On the second mount plate 109, the part of the plurality of slides excluding the one end portion is mounted. The first mount plate 108 and the second mount plate 109 are separated, and a gap is formed between the first mount plate 108 and the second mount plate 109. The first mount plate 108 and the second mount plate 109 separated from each other are at least partially connected by one or more ribs 110. The one or more ribs 110 are formed of a material that has a flexibility when formed to be thin and has a rigidity when formed to have a predetermined thickness or more (e.g., synthetic resin). Specifically, the one or more ribs 110 are formed thin enough in the Z direction so as to enable the first mount plate 108 and the second mount plate 109 to be bent relatively when the ribs 110 are bent.

On the second mount plate 109, an operation portion 111 for a user to operate with a finger is provided. The operation portion 111 is a hollow bump that rises from the second mount plate 109. The operation portion 111 is provided at, for example, the center of the second mount plate 109 in the Y direction. For example, the length of the operation portion 111 in the X direction is the same as that of the second mount plate 109 in the X direction, and the width thereof in the Y direction is set such that the user can easily operate it with his/her finger. The height of the operation portion 111 in the Z direction and that of the plurality of partitions 102 in the Z direction are the same or almost the same. An operation piece (operation piece 140 in FIG. 9) is internally provided at a predetermined position of the operation portion 111 near the first accommodation portion 106. The operation piece 140 protrudes in the Z direction in the hollow portion of the operation portion 111.

The plurality of partitions 102 each include a first partition 113 provided in the first accommodation portion 106 and a second partition 114 provided in the second accommodation portion 107. The first partition 113 and the second partition 114 are separated.

The pair of first outer frames 104 have the same structure. Therefore, in the descriptions below, unless there is a need to distinguish the pair of first outer frames 104 from each other, the first outer frames 104 will be referred to as "first outer frame 104", and descriptions will be given on a single first outer frame 104. The first outer frame 104 includes a first frame portion 115 located in the first accommodation portion 106 and a second frame portion 116 located in the second accommodation portion 107. The first frame portion 115 and the second frame portion 116 are separated with a gap in between, for example. A first notch 118 is formed at a part of an end portion of the first frame portion 115 (referred to as "first end portion 117") opposing the second frame portion 116, the part protruding downwardly from the mount plate 101. The first notch 118 is tapered in such a manner that a distance from the second frame portion 116 becomes larger as it comes farther away from the mount plate 101 in the Z direction. A second notch 120 is provided at a part of an end portion of the second frame portion 116 (referred to as "second end portion 119") opposing the first frame portion 115, the part protruding downwardly from the mount plate 101. The second notch 120 is tapered in such a manner that a distance from the first frame portion 115 becomes larger as it comes farther away from the mount plate 101 in the Z direction. More specifically, assuming that the ribs 110 are bent and thus the first mount plate 108 and the second mount plate 109 are relatively bent so as to form an angle on a lower surface side, the first notch 118 and the second notch 120 are formed such that the first end portion 117 and the second end portion 119 do not interfere with each other up to a predetermined angle. A cylindrical first boss 122 protruding in the Y direction is provided at an end portion of the first frame portion 115 on the other side of the first end portion 117 (referred to as "third end portion 121"). A cylindrical second boss 124 protruding in the Y direction is provided at an end portion of the second frame portion 116 on the other side of the second end portion 119 (referred to as "fourth end portion 123"). A Z-direction distance between a center axis of the first boss 122 and the mount plate 101 is the same as that between a center axis of the second boss 124 and the mount plate 101.

2.2. Structure of Frame

Figure 5:
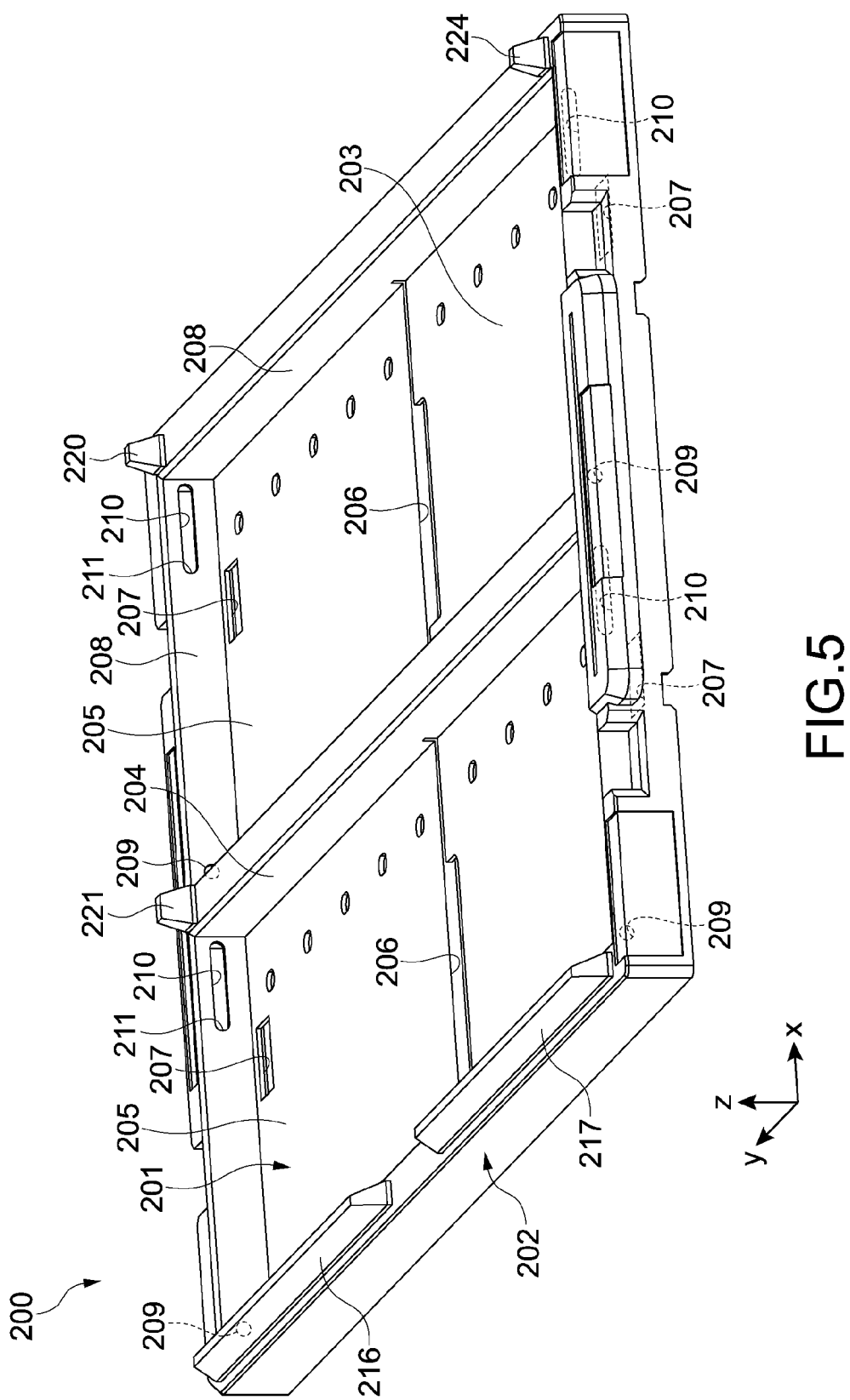
FIG. 5 is a perspective view of a frame.
Figure 6:
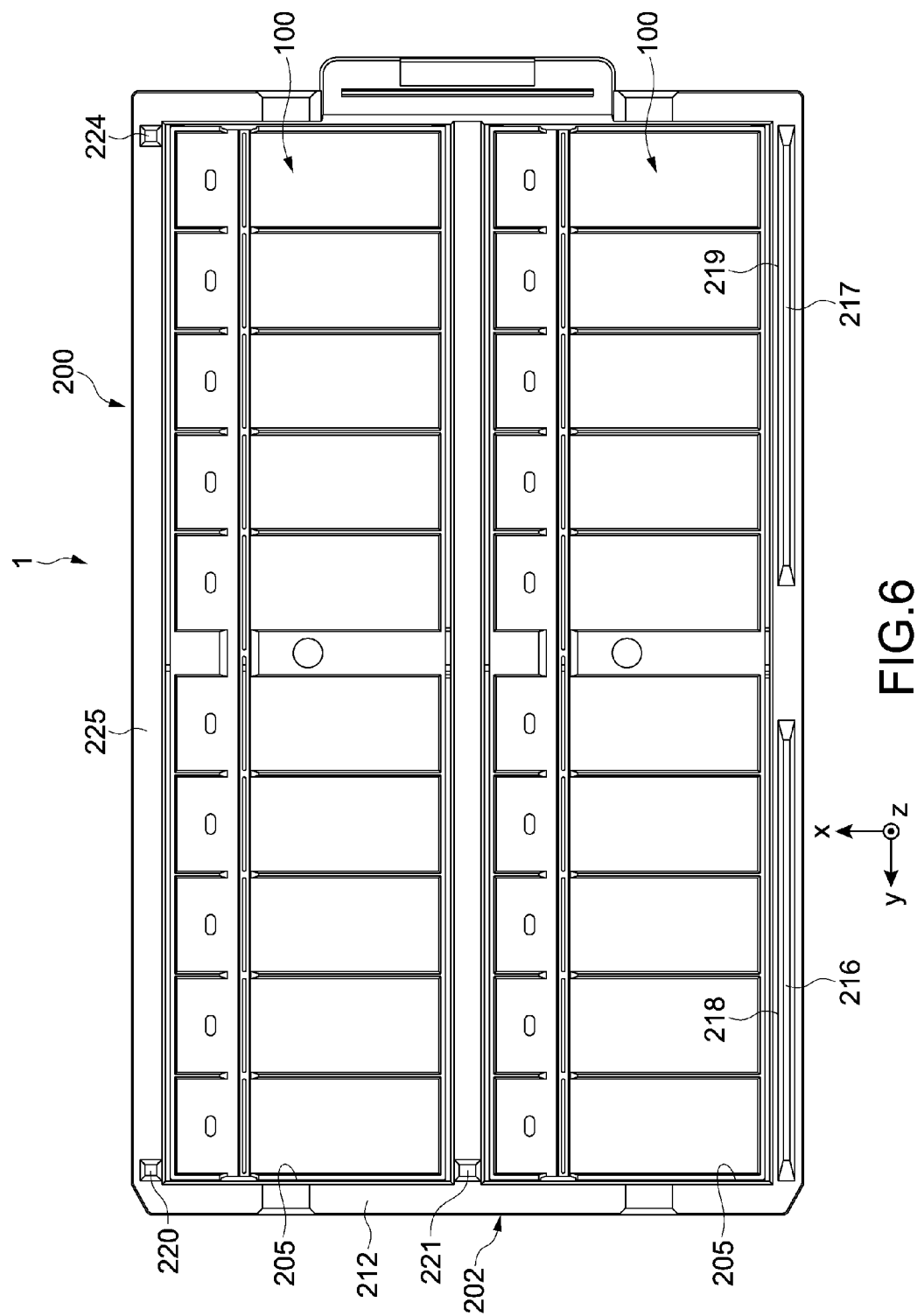
FIG. 6 is a top view of the slide tray.

FIG. 5 is a perspective view of the frame 200. FIG. 6 is a top view of the slide tray 1.

The frame 200 includes a setup plate 201 and a frame outer frame 202. The setup plate 201 is rectangular. On an upper surface 203 of the setup plate 201, the one or more slide accommodation portions 100 (see FIG. 6) are set. The frame outer frame 202 protrudes from the upper surface 203 of the setup plate 201 in the Z direction.

The upper surface 203 of the setup plate 201 is sectioned into two setup areas 205 by a frame partition 204. The one or more (two in this example) slide accommodation portions 100 are set in the two setup areas 205. The two setup areas 205 have the same structure. Therefore, in the descriptions below, descriptions will be given on a single setup area 205. In the setup area 205, at a position that opposes the operation portion 111 of the slide accommodation portion 100 when the slide accommodation portion 100 is set in the setup area 205, a first through-hole 206 is provided. Specifically, the first through-hole 206 is formed at a position and in a shape at/with which the flip-up portion 300 provided on a lower surface of the setup plate 201 (lower surface 236 in FIG. 7) protrudes toward the setup area 205 to be accommodated in the hollow operation portion 111.

At two arbitrary positions of the setup area 205 that oppose the second mount plate 109 of the slide accommodation portion 100 when the slide accommodation portion 100 is set in the setup area 205, two second through-holes 207 are formed. For example, the second through-holes 207 are formed to be line-symmetric with respect to a center line (symmetry axis) of the setup plate 201 extending in the X direction and also have a line-symmetric shape. For example, the two second through-holes 207 are formed at positions close to the frame outer frame 202 in the Y direction. The two second through-holes 207 are formed in a shape and at positions with/at which two arms (to be described later) of a slide conveyor apparatus (to be described later) can partially pass.

The frame outer frame 202 protrudes from the upper surface 203 of the setup plate 201 in the Z direction and sections, surrounds, and restricts each of the one or more slide accommodation portions 100 set in the setup plate 201. The frame outer frame 202 surrounds the circumference of the rectangular setup plate 201 and is rectangular as a whole. When the slide accommodation portion 100 is set in the setup area 205, the first outer frames 104 and second outer frames 105 of the slide accommodation portions 100 come into contact with inner walls 208 of the frame outer frame 202. The Z-direction height of the frame outer frame 202 is equal to or larger than that of the slide accommodation portions 100.

At a part of the inner walls 208 of the frame outer frame 202 that oppose the second bosses 124 provided on the first outer frames 104 of the slide accommodation portion 100 when the slide accommodation portion 100 is set in the setup area 205, round holes 209 that sink in the Y direction are formed. The diameter of the round holes 209 is slightly larger than that of the second boss 124. The round holes 209 are each capable of rotatably holding the second boss 124. On the other hand, at a part of the inner walls 208 of the frame outer frame 202 that oppose the first bosses 122 provided on the first outer frames 104 of the slide accommodation portion 100 when the slide accommodation portion 100 is set in the setup area 205, long holes 210 that sink in the Y direction are formed. The long holes 210 are long in the X direction. The Z-direction width of the long holes 210 is slightly larger than the diameter of the first bosses 122. The long holes 210 are capable of holding the first bosses 122 such that the first bosses 122 are rotatable and movable in the X direction. More specifically, when the slide accommodation portion 100 is set in the setup area 205, the second boss 124 of the slide accommodation portion 100 is held by the round hole 209, and the first boss 122 is held by the long hole 210. At this time, there is a predetermined distance between an end 211 of the long hole 210 near the round hole 209 and the first boss 122.

2.2.1. Plurality of Convex Portions

On an upper surface 212 of the frame outer frame 202, a plurality of convex portions are formed. The plurality of convex portions each protrude from the upper surface 212 of the frame outer frame 202 in the Z direction. When the slide accommodation portion 100 is set in the setup area 205, the Z-direction height of the plurality of convex portions is larger than that of the slide accommodation portion 100. In this example, convex portions 216, 217, 220, 221, and 224 are formed on the upper surface 212 of the frame outer frame 202.

Figure 7:
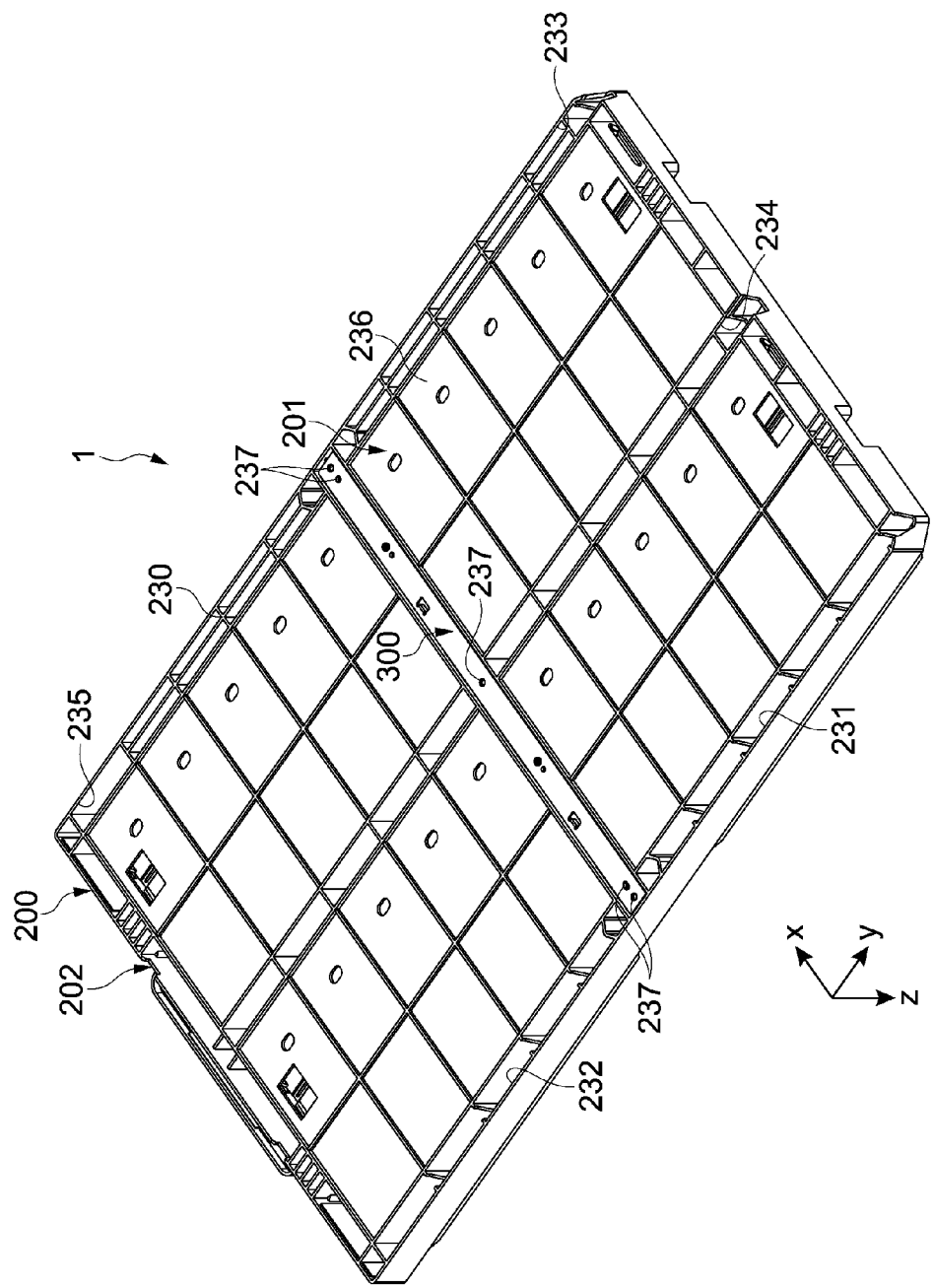
FIG. 7 is a bottom perspective view of the slide tray.

FIG. 7 is a bottom perspective view of the slide tray 1.

At positions on a lower surface 230 of the frame outer frame 202 opposing the convex portions 216, 217, 220, 221, and 224, at least one concave portion that sinks in the Z direction is formed. In this example, concave portions 231, 232, 233, 234, and 235 are formed on the lower surface 230 of the frame outer frame 202 at positions opposing the convex portions 216, 217, 220, 221, and 224. The Z-direction depth of the concave portions 231, 232, 233, 234, and 235 is equal to or larger than the Z-direction protrusion length of the convex portions 216, 217, 220, 221, and 224. More specifically, the concave portions 231, 232, 233, 234, and 235 are capable of fully accommodating convex portions having the same shape as the opposing convex portions 216, 217, 220, 221, and 224.

One or more bosses 237 are formed on the lower surface 236 of the setup plate 201 of the frame 200 for positioning the flip-up portion 300 on the frame 200. The one or more bosses protrude from the lower surface 236 of the setup plate 201 of the frame 200 in the Z direction. Specifically, the one or more bosses are formed at/in positions and shape at/with which the bosses can be inserted into one or more through-holes (to be described later) of a base 310 of the flip-up portion 300 set on a second surface as a back surface of the setup plate 201.

2.2.2. Slide Tray Stack

The slide tray 1 including the frame 200 having the structure as described above can be plurally stacked in the Z direction. Specifically, the convex portions 216, 217, 220, 221, and 224 of one slide tray 1 (lower-side slide tray 1) are fit in the concave portions 231, 232, 233, 234, and 235 of another slide tray 1 (upper-side slide tray 1). In this case, the lower surface 230 of the frame outer frame 202 of the upper-side slide tray 1 comes into contact with the upper surface 212 of the frame outer frame 202 of the lower-side slide tray 1. As a result, the upper-side slide tray 1 is held horizontally by the lower-side slide tray 1. Here, since the Z-direction height of the frame outer frame 202 is equal to or larger than that of the slide accommodation portion 100, even when a plurality of slide trays 1 are stacked while slides are accommodated in the slide accommodation portion 100, the upper-side slide tray 1 does not interfere with the slides accommodated in the lower-side slide tray 1.

As described above, the plurality of convex portions 216, 217, 220, 221, and 224 and the plurality of concave portions 231, 232, 233, 234, and 235 provided apart from one another fit. As a result, the plurality of convex portions 216, 217, 220, 221, and 224 and the plurality of concave portions 231, 232, 233, 234, and 235 become a stacking guide so that the plurality of slide trays 1 can be easily stacked while aligned in the three XYZ directions. Moreover, since the plurality of convex portions 216, 217, 220, 221, and 224 and the plurality of concave portions 231, 232, 233, 234, and 235 fit, fitting is secure. Consequently, the slide trays 1 can be stacked with high stability, and thus there is less possibility of collapsing.

2.3. Structure of Flip-up Portion

Figure 8:
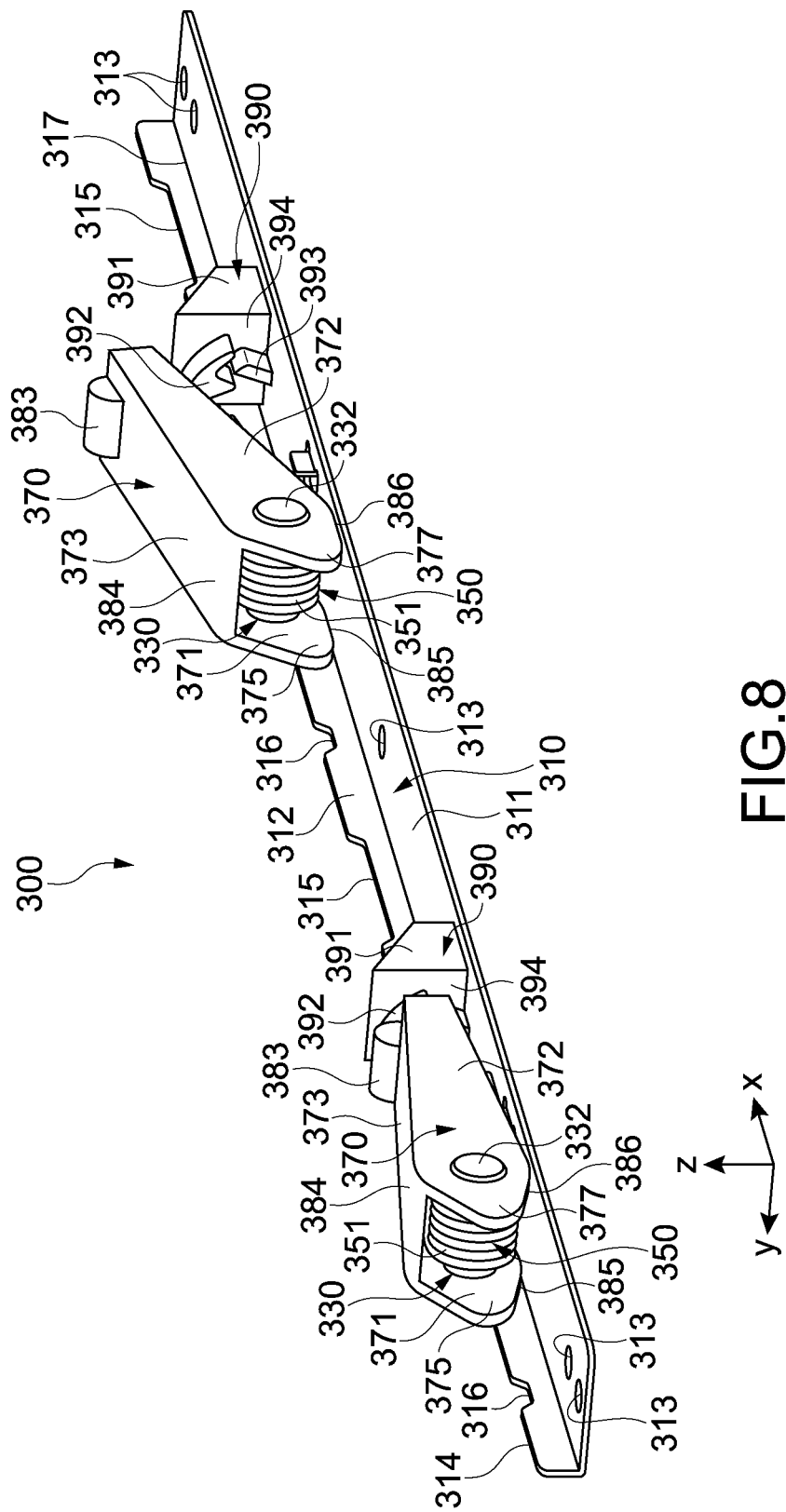
FIG. 8 is a perspective view of a flip-up portion.
Figure 9:
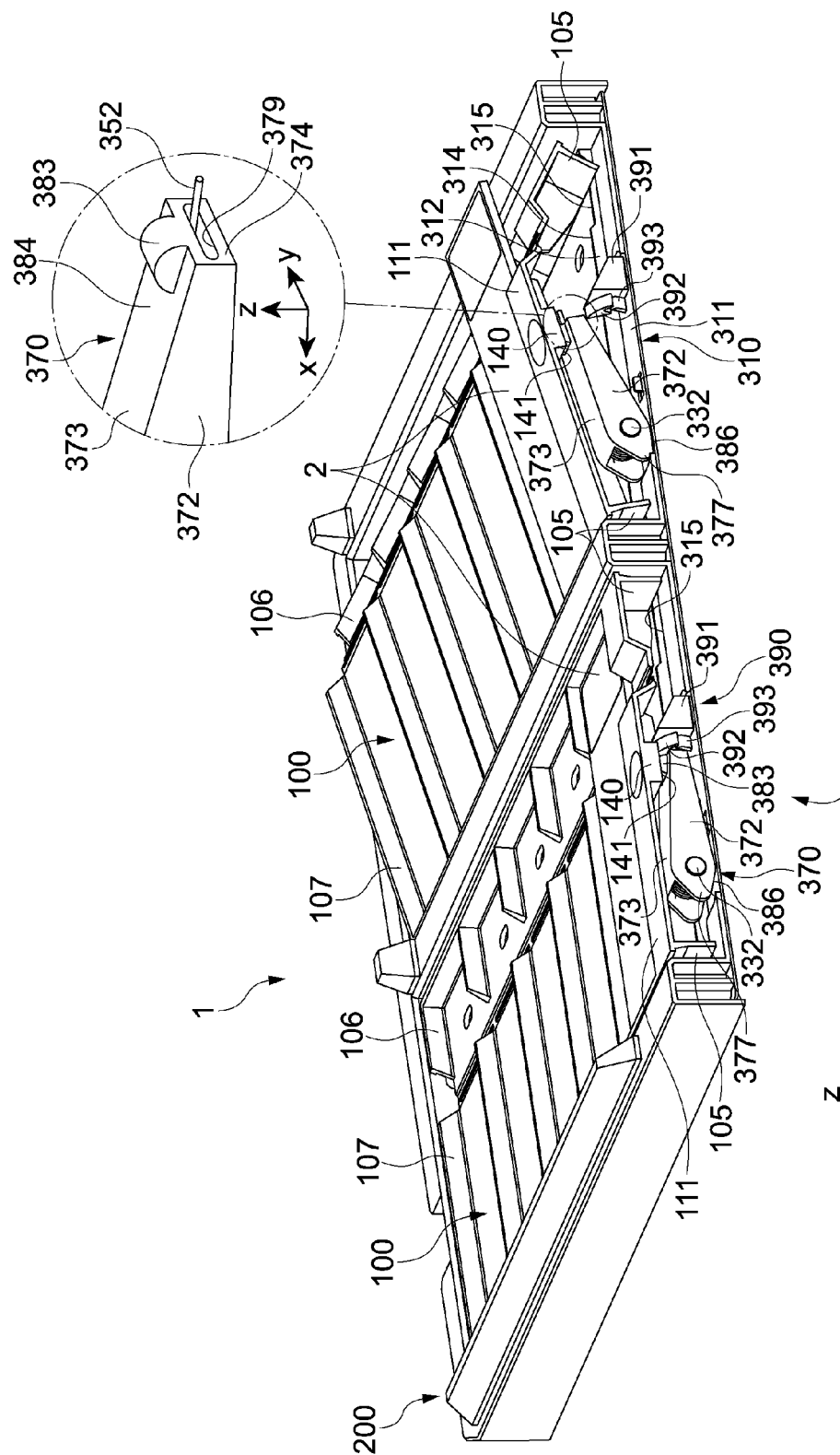
FIG. 9 is a cross-sectional diagram of the slide tray accommodating the plurality of slides and a partially-enlarged diagram showing a part of the flip-up portion from a different angle, the diagrams showing a positional relationship between the flip-up portion and the slide accommodation portion.

FIG. 8 is a perspective view of the flip-up portion 300. FIG. 9 is a cross-sectional diagram of the slide tray 1 accommodating the plurality of slides 2 and a partially-enlarged diagram showing a part of the flip-up portion 300 from a different angle, the diagrams showing a positional relationship between the flip-up portion 300 and the slide accommodation portion 100.

The flip-up portion 300 includes a base 310 and two sets of shafts 330, springs 350, arms 370, and cam portions 390. The two sets of shafts 330, springs 350, arms 370, and cam portions 390 have the same respective structures. Therefore, hereinafter, descriptions will be given on one set of shaft 330, spring 350, arm 370, and cam portion 390.

2.3.1. Structure of Base

The base 310 includes a bottom plate 311 and a side plate 312. The bottom plate 311 has a long and thin rectangular shape with a small width. The length of long sides of the rectangular bottom plate 311 is equal to or smaller than the width of the frame 200 in the X direction. The bottom plate 311 is set in the frame 200 such that the long sides extend in the X direction, the short sides extend in the Y direction, and the bottom plate 311 opposes the two operation portions 111 of the slide accommodation portions 100. On the bottom plate 311, one or more through-holes 313 for positioning the flip-up portion 300 with respect to the frame 200 are formed. The one or more bosses 237 (see FIG. 7) provided on the lower surface 236 of the setup plate 201 of the frame 200 are inserted into the one or more through-holes 313. As a result, the flip-up portion 300 is positioned with respect to the frame 200. In such a positioned state, the base 310 is fixed to the frame 200 with an adhesive tape or the like.

The side plate 312 is tilted in the Z direction so as to be bent orthogonally from one long side 317 of the bottom plate 311. At an upper end portion 314 of the side plate 312 in the Z direction, two sets of first notches 315 and second notches 316 are formed. The two sets of first notches 315 and second notches 316 have the same respective shapes and same positional relationship. Therefore, descriptions below will be given on one set of first notch 315 and second notch 316. The first notch 315 is formed at/in a position and shape at/with which the second outer frame 105 located in the first accommodation portion 106 of the slide accommodation portion 100 does not come into contact with the side plate 312 when the flip-up portion 300 and the slide accommodation portions 100 are set in the frame 200. In addition, the second notch 316 is formed at/in a position and shape at/with which the second outer frame 105 located in the second accommodation portion 107 of the slide accommodation portion 100 does not come into contact with the side plate 312 at this time. More specifically, the first bosses 122 (see FIG. 4) of the slide accommodation portion 100 rotate in the long holes 210 (see FIG. 5) of the frame 200 and move in the X direction. At this time, the first notch 315 is formed at/in a position and shape at/with which the second outer frame 105 located in the first accommodation portion 106 is constantly in a non-contact state with the side plate 312. Moreover, the second notch 316 is formed at/in a position and shape at/with which the second outer frame 105 located in the second accommodation portion 107 is constantly in a non-contact state with the side plate 312 when the second bosses 124 (see FIG. 4) of the slide accommodation portion 100 rotate in the round holes 209 (see FIG. 5) of the frame 200.

2.3.2. Structure of Shaft

The shaft 330 is cylindrical, provided between the first notch 315 and the second notch 316 of the side plate 312 of the base 310, protrudes from the side plate 312 in the Y direction, and opposes the bottom plate 311 of the base 310 in a non-contact state.

2.3.3. Structure of Spring

The spring 350 includes a coil portion 351 wound in a cylindrical spiral and an operation pin 352 (see partially-enlarged diagram of FIG. 9) linearly extending from one end of the coil portion 351. An inner diameter of the cylindrical coil portion 351 is larger than the diameter of the cylindrical shaft 330.

2.3.4. Structure of Arm

Figure 10:
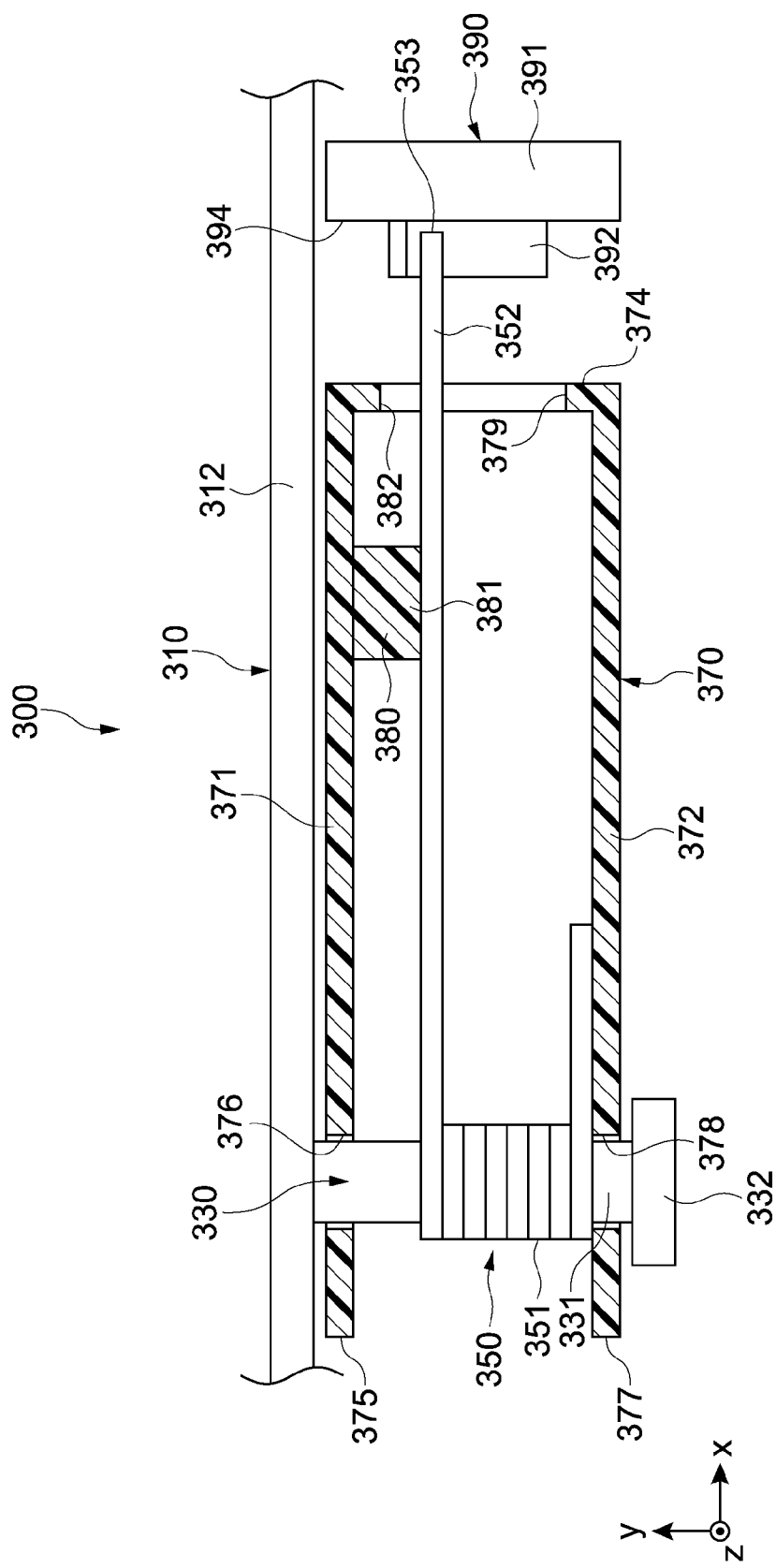
FIG. 10 is a schematic diagram showing a positional relationship among a set of a shaft, spring, arm, and cam portion.

FIG. 10 is a schematic diagram showing a positional relationship among one set of the shaft 330, spring 350, arm 370, and cam portion 390. Hereinafter, descriptions will be given with reference to FIGS. 8, 9, and 10.

The arm 370 includes a first side plate 371, a second side plate 372, a coupling plate 373, and a tip end plate 374. The coupling plate 373 couples the first side plate 371 and the second side plate 372 such that the first side plate 371 and the second side plate 372 generally oppose each other. At one end portion 375 of the first side plate 371, a circular first through-hole 376 is formed. At one end portion 377 of the second side plate 372, a circular second through-hole 378 is formed. Inner diameters of the circular first through-hole 376 and second through-hole 378 are the same and larger than the diameter of the cylindrical shaft 330 but smaller than the inner diameter of the cylindrical coil portion 351. A distance between the first side plate 371 and the second side plate 372 is smaller than the length of the cylindrical shaft 330 in the axial direction (Y direction) and larger than the width of the cylindrical coil portion 351 in the axial direction (Y direction).

Referring to FIG. 10, the shaft 330 protruding from the side plate 312 of the base 310 in the Y direction is inserted into the first through-hole 376 of the first side plate 371 of the arm 370, the coil portion 351 of the spring 350, and the second through-hole 378 of the second side plate 372 of the arm 370 in order from the side plate 312 side of the base 310. As a result, the shaft 330 rotatably holds the arm 370 and the spring 350. At a tip end 331 of the shaft 330, a cap 332 having a diameter larger than the inner diameter of the second through-hole 378 is provided. The cap 332 restricts movements of the arm 370 and the spring 350 in the Y direction (direction that moves farther away from side plate 312). At the same time, the cap 332 suppresses a bias force of the spring 350 in the Y direction (direction that moves farther away from side plate 312).

Referring to the partially-enlarged diagram of FIG. 9, the tip end plate 374 of the arm 370 is provided at a tip end of the arm 370 (end portion distant from shaft 330 in X direction). A long hole 379 is formed on the tip end plate 374. The long hole 379 penetrates the tip end plate 374 in the direction orthogonal to the axial direction of the shaft 330 (Y direction) and is elongated in the axial direction of the shaft 330 (Y direction). The operation pin 352 of the spring 350 protrudes from the long hole 379 to be exposed from the arm 370.

Referring to FIG. 10, a positioning protrusion 380 is provided on an inner surface of the first side plate 371 of the arm 370. The positioning protrusion 380 protrudes toward the second side plate 372 in the Y direction. A Y-direction tip end surface 381 of the positioning protrusion 380 is closer to the second side plate 372 in the Y direction than an end portion 382 of the long hole 379 on the first side plate 371 side. The Y-direction tip end surface 381 of the positioning protrusion 380 is formed at/in a position and shape at/with which the operation pin 352 of the spring 350 is constantly in contact therewith. The operation pin 352 of the spring 350 causes a bias force in the Y direction (specifically, direction that approaches first side plate 371), but such a bias force is suppressed by the positioning protrusion 380 protruding in the Y direction. By the positioning protrusion 380, the operation pin 352 penetrating the long hole 379 is positioned closer to the second side plate 372 in the Y direction than the end portion 382 of the long hole 379 on the first side plate 371 side in the long hole 379.

Referring to the partially-enlarged diagram of FIG. 9, a semi-cylindrical sliding protrusion 383 is provided on the tip end plate 374 side of the coupling plate 373 of the arm 370. The sliding protrusion 383 protrudes from an upper surface 384 of the coupling plate 373 in a direction orthogonal to the upper surface 384 of the coupling plate 373. The axial center of the semi-cylindrical sliding protrusion 383 extends in the Y direction.

Referring to the cross-sectional diagram of FIG. 9, the arm 370 is designed such that the sliding protrusion 383 of the arm 370 opposes a front surface 141 (lower surface) of the operation piece 140 of the slide accommodation portion 100 in a contact or non-contact state and other portions of the arm 370 are not in contact with the slide accommodation portion 100. The operation pin 352 of the spring 350 causes a bias force in the Z direction (specifically, direction that approaches operation piece 140 of slide accommodation portion 100), but such a bias force is suppressed by the operation piece 140 protruding in the Z direction.

Further, the arm 370 is formed to be capable of rotating a predetermined angle about the center axis of the shaft 330 and restricting it from rotating more than the predetermined angle. Specifically, the arm 370 is formed such that, when the ribs 110 of the slide accommodation portion 100 are bent and thus the first mount plate 108 and the second mount plate 109 are relatively bent so as to form an angle on the lower surface side, the first side plate 371 and the second side plate 372 do not interfere with the bottom plate 311 of the base 310. The arm 370 is also formed such that, while bending of the first mount plate 108 and the second mount plate 109 is restricted, the arm 370 does not rotate more than that. In this example, a first notch 385 (see FIG. 8) is formed at the one end portion 375 of the first side plate 371 on the other side of the tip end plate 374 with respect to the axial center of the first through-hole 376, at a position opposing the bottom plate 311 of the base 310. In addition, a second notch 386 is formed at one end portion 377 of the second side plate 372 on the other side of the tip end plate 374 with respect to the second through-hole, at a position opposing the bottom plate 311 of the base 310.

2.3.5. Structure of Cam Portion

The cam portion 390 includes a cam base 391, a heart cam 392, and a restriction piece 393.

The cam base 391 is fixed to the bottom plate 311 of the base 310. Specifically, the cam base 391 is formed at/in a position and shape at/with which the cam base 391 opposes the tip end plate 374 of the arm 370 and does not interfere with the slide accommodation portion 100.

The heart cam 392 is provided on a cam surface 394 of the cam base 391 opposing the tip end plate 374 of the arm 370. Specifically, the heart cam 392 is provided at a position at which the operation pin 352 protruding from the tip end plate 374 of the arm 370 can trace the circumference of the heart cam 392. The heart cam 392 is formed in a shape that enables the heart cam 392 to hold the operation pin 352 at a lock position, define an unlock path that the operation pin 352 traces to reach an unlock position, and define a lock path that the operation pin 352 traces again to reach the lock position.

The restriction piece 393 is provided on the cam surface 394 of the cam base 391. Specifically, the restriction piece 393 helps the operation pin 352 trace the circumference of the heart cam 392. In other words, the restriction piece 393 restricts the operation pin 352 from deviating from the lock path and the unlock path or restricts the operation pin 352 from tracing in the opposite direction from the lock path and the unlock path.

Figure 11:
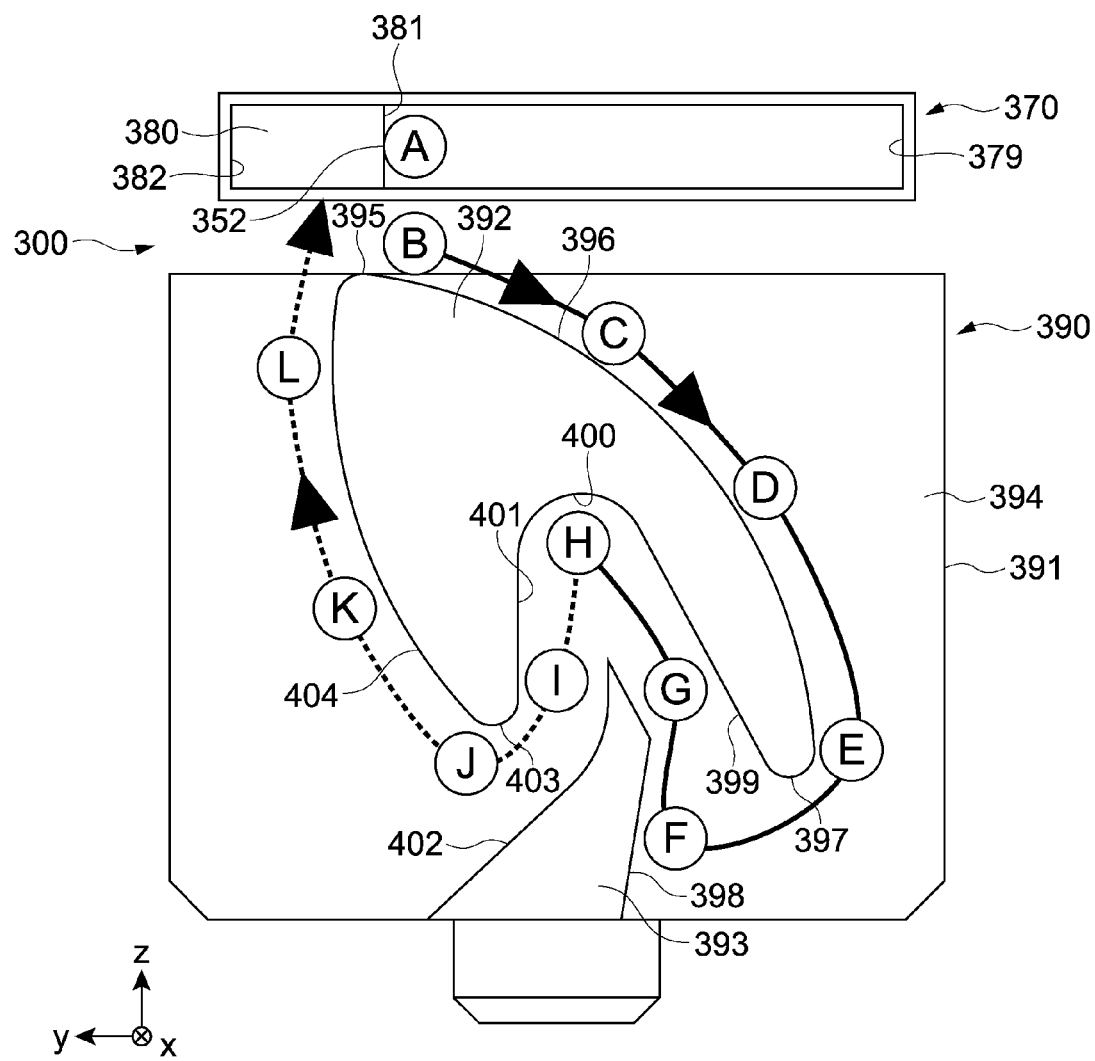
FIG. 11 is a schematic diagram for explaining moves of an operation pin.

FIG. 11 is a schematic diagram for explaining moves of the operation pin 352.

Specific examples of the shapes of the heart cam 392 and the restriction piece 393 and moves of the operation pin 352 of the spring 350 will be described. Points A to L in the figure schematically indicate positions of the operation pin 352, and lines connecting Points A to L schematically indicate a path of a center point of a tip end 353 of the operation pin 352. Solid lines indicate the lock path, and broken lines indicate the unlock path. It should be noted that for convenience, the longitudinal and lateral directions on the figure are referred to as "upward direction", "downward direction", "left-hand direction", and "right-hand direction" as appropriate. The longitudinal direction corresponds to the Z direction, whereas the lateral direction corresponds to the Y direction.

First, when the operation pin 352 is at the unlock position (A), the operation pin 352 is biased in the upward and left-hand directions. The bias force in the upward direction is suppressed by the operation piece 140 (not shown) of the slide accommodation portion 100. The bias force in the left-hand direction is suppressed by the positioning protrusion 380 of the arm 370. By the positioning protrusion 380, the operation pin 352 is positioned at a position biased in the protrusion direction of the positioning protrusion 380 (right-hand direction) with respect to a first apex portion 395 of the heart cam 392.

The lock path will be described. When the operation pin 352 is at the unlock position (A), the operation pin 352 moves downwardly as the operation portion 111 of the slide accommodation portion 100 is pressed downwardly to thus come into contact with a first side 396 of the heart cam 392 (B). While being in contact with the first side 396 of the heart cam 392, the operation pin 352 moves downwardly by the pressing force, and at the same time, moves in the right-hand direction in the long hole 379 (C, D). Upon reaching a second apex portion 397 of the heart cam 392 (E), the operation pin 352 breaks away from the heart cam 392. The operation pin 352 is released from the force that suppresses the bias force by the heart cam 392 in the left-hand direction, moves in the left-hand direction in the long hole 379 using the bias force in the left-hand direction, and thus reaches a first side 398 of the restriction piece 393 (F). The operation pin 352 that has reached the first side 398 of the restriction piece 393 is released from the force that suppresses the upward bias force by the heart cam 392 and moves along the first side 398 of the restriction piece 393 using the upward bias force. Upon release from the first side 398 of the restriction piece 393, the operation pin 352 comes into contact with a second side 399 of the heart cam 392 by the upward bias force (G) and reaches a valley portion 400 of the heart cam 392 by the upward bias force while being in contact with the second side 399 (H). The operation pin 352 that has reached the valley portion 400 is positioned as a result of the bias forces in the upward and left-hand directions being suppressed by the valley portion 400 of the heart cam 392. The position (H) is the lock position of the operation pin 352.

Next, the unlock path will be described. When the operation portion 111 of the slide accommodation portion 100 is pressed downwardly at the time the operation pin 352 is at the lock position (H), the operation pin 352 moves downwardly by the pressing force while being in contact with a third side 401 of the heart cam 392 by the leftward bias force and being guided in the left-hand direction by a second side 402 of the restriction piece 393 (I). Upon reaching a third apex portion 403 of the heart cam 392 (J), the operation pin 352 is released from the force that suppresses the upward and leftward bias forces by the third side 401 of the heart cam 392. While being in contact with a fourth side 404 of the heart cam 392, the operation pin 352 moves by the upward bias force (K, L) to be positioned at the unlock position (A).

3. Moves of Slide Tray

Next, moves of the slide tray 1 structured as described above will be described. First, moves of the slide tray 1 when it changes from a non-tilted state to a tilted state will be described. Then, moves of the slide tray 1 when it changes from the tilted state to the non-tilted state will be described.

3.1. Moves of Slide Tray when it Changes from Non-tilted State to Tilted State

Figure 12:
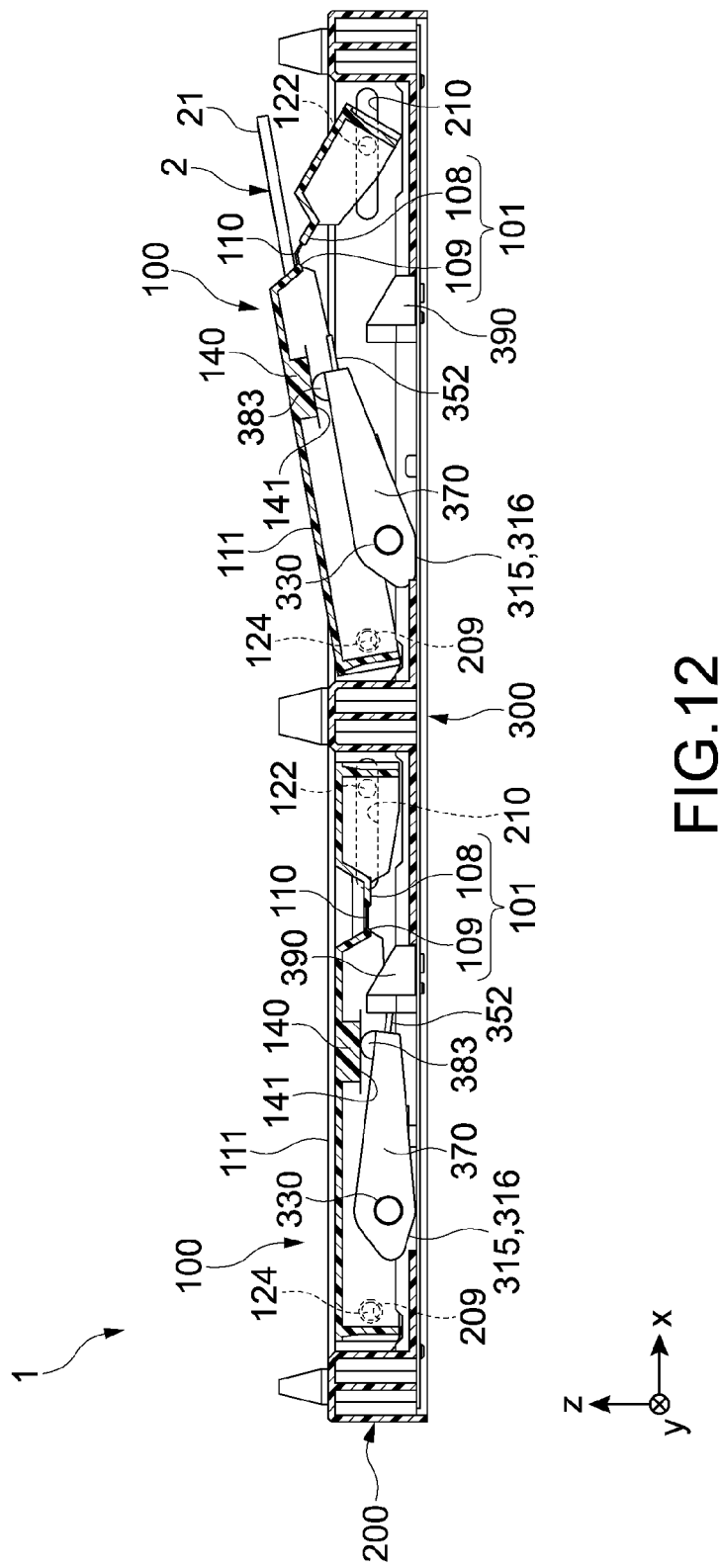
FIG. 12 is a schematic diagram showing a non-tilted slide accommodation portion and a tilted slide accommodation portion.

FIG. 12 is a schematic diagram showing a non-tilted slide accommodation portion 100 and a tilted slide accommodation portion 100.

When the slide accommodation portion 100 is in a non-tilted state (left-hand side in figure), the operation pin 352 of the flip-up portion 300 is at the lock position. When the operation pin 352 is at the lock position, the operation piece 140 of the slide accommodation portion 100 opposes the sliding protrusion 383 of the arm 370 in a contact or non-contact state. As a pressing force in the Z direction is imparted to the operation portion 111 of the slide accommodation portion 100 by a finger of a user or the like, the operation pin 352 at the lock position moves to the unlock position. When the operation pin 352 moves to the unlock position, the arm 370 rotates about the shaft 330. At this time, the sliding protrusion 383 of the arm 370 lifts up the operation piece 140 in at least the Z direction while sliding on the front surface 141 of the operation piece 140 of the slide accommodation portion 100. As the operation piece 140 is lifted up, the ribs 110 are bent to relatively bend the first mount plate 108 and the second mount plate 109 such that an angle is formed on the lower surface side. At this time, the second bosses 124 of the slide accommodation portion 100 rotate in the round holes 209 of the frame 200. At the same time, the first bosses 122 rotate in the long holes 210 and move in the direction that approaches the second bosses 124. As the arm 370 rotates a predetermined angle, the first and second notches 316 of the arm 370 come into contact with the bottom plate 311 of the base to thus restrict the arm 370 from further rotating. As a result, the slide accommodation portion 100 is positioned in a tilted state (right-hand side in figure).

It should be noted that the flip-up portion 300 only needs to be designed such that, when the slide accommodation portion 100 is positioned in the tilted state, an angle between the setup plate 201 of the frame 200 and the second mount plate 109 of the slide accommodation portion 100 becomes, for example, about 10 degrees. About 10 degrees is a value with which the user can easily insert a finger between the slide 2 mounted on the second mount plate 109 and the first mount plate 108.

3.2. Moves of Slide Tray when it Changes from Tilted State to Non-tilted State When the slide accommodation portion 100 is at the tilted position, the operation pin 352 of the flip-up portion 300 is at the unlock position. When the operation pin 352 is at the unlock position, the operation piece 140 of the slide accommodation portion 100 is in contact with the sliding protrusion 383 of the arm 370. As a pressing force in the Z direction is imparted to the operation portion 111 of the slide accommodation portion 100 by a finger of the user or the like, the bent ribs 110 of the slide accommodation portion 100 become flat, and thus the first mount plate 108 and the second mount plate 109 that have been relatively bent become flat again. At this time, the second bosses 124 of the slide accommodation portion 100 rotate in the round holes 209 of the frame 200. At the same time, the first bosses 122 rotate in the long holes 210 and move in the direction that moves away from the second bosses 124. By the pressing force imparted to the operation portion 111 in the Z direction, the sliding protrusion 383 of the arm 370 that is in contact with the operation portion 111 is pressed down. The sliding protrusion 383 of the arm 370 moves at least downwardly in the Z direction while sliding on the front surface 141 of the operation piece 140 of the slide accommodation portion 100. As the arm 370 moves downwardly in the Z direction and the operation pin 352 comes into contact with the cam portion 390, the operation pin 352 moves from the unlock position to the lock position by the pressing force in the Z direction to be restrained at the lock position. As a result, the slide accommodation portion 100 is positioned in the non-tilted state.

4. Application of Slide Tray to Slide Conveyor Apparatus

In the descriptions above, the slide accommodation portion 100 is switched between the tilted state and the non-tilted state as the operation portion 111 of the slide tray 1 is pressed with a finger of the user or the like. However, the slide conveyor apparatus may switch the slide accommodation portion 100 between the tilted state and the non-tilted state.

4.1. Outline of Slide Conveyor Apparatus

A scanner apparatus that scans and digitizes a large number of slides is known. In scanning the slides using the scanner apparatus, it is general to manually move the large number of slides accommodated in the slide tray to a cassette dedicated for the scanner apparatus. Moving the large number of slides one by one is a laborious task.

There are at least two types of cassettes dedicated for the scanner apparatus. One is a type that accommodates a plurality of slides that are arranged in parallel while flat surfaces of the slides oppose one another, and the other is a type that accommodates a plurality of slides that are arranged longitudinally and laterally while the plurality of slides are mounted on a mount plate as in the slide tray. In the latter type, as in the slide tray, four sides of a slide are surrounded by partitions for sectioning the plurality of adjacent slides from one another. In the former type of cassette, since the flat surfaces of the slides oppose one another, there is a drawback that segments mounted on the slides cannot be visually checked. On the other hand, while visibility is fine in the latter type of cassette, since the slides are surrounded by partitions, it is difficult for the grip mechanism of the scanner apparatus to grip the slides to take it out.

In view of the circumstances as described above, it is another object of the present disclosure to eliminate the task of manually moving the slides accommodated in the slide tray to a dedicated cassette. In addition, it is still another object of the present disclosure to provide a slide conveyor apparatus capable of easily taking out the slides accommodated in the slide tray having fine visibility.

4.2. Structure of Slide Conveyor Apparatus

Figure 13:
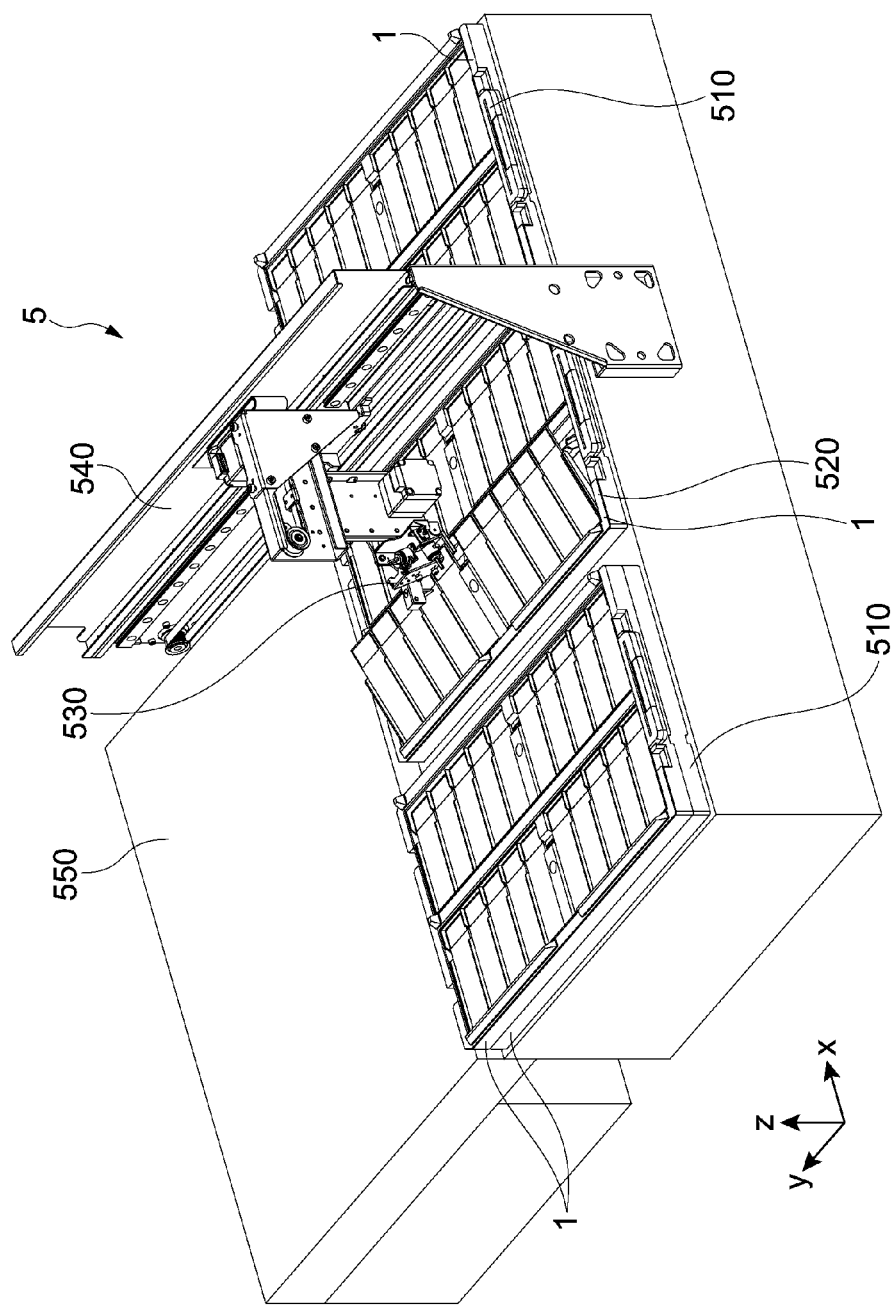
FIG. 13 is a schematic diagram showing a slide conveyor apparatus according to the embodiment.

FIG. 13 is a schematic diagram showing the slide conveyor apparatus according to this embodiment. In the specification, the phrase "slide conveyor apparatus" refers to an apparatus capable gripping slides accommodated in the slide tray, taking the slides out, and conveying the slides. A specific example of the slide conveyor apparatus is a scanner apparatus that scans and digitizes slides.

The slide conveyor apparatus 5 of this embodiment includes slide tray load portions 510, a slide tray setup portion 520, a lift-up portion (lift-up portion 560 of FIG. 14), a grip portion 530, a conveyor portion 540, and a scanner portion 550. One or more slide trays 1 of the embodiment above are loaded (stacked) on the slide tray load portions 510. A slide tray conveyor portion (not shown) takes out the slide tray 1 accommodating a slide to be scanned out of the one or more slide trays 1 loaded on the slide tray load portions 510 and sets the slide tray 1 on the slide tray setup portion 520. The lift-up portion 560 (see FIG. 14) switches the slide accommodation portion 100 of the slide tray 1 set on the slide tray setup portion 520 between the non-tilted state and the tilted state. The grip portion 530 grips the slide accommodated in the tilted slide accommodation portion 100. The conveyor portion 540 conveys the grip portion 530 between the slide tray setup portion 520 and the scanner portion 550.

4.2.1. Lift-up Portion

Figure 14:
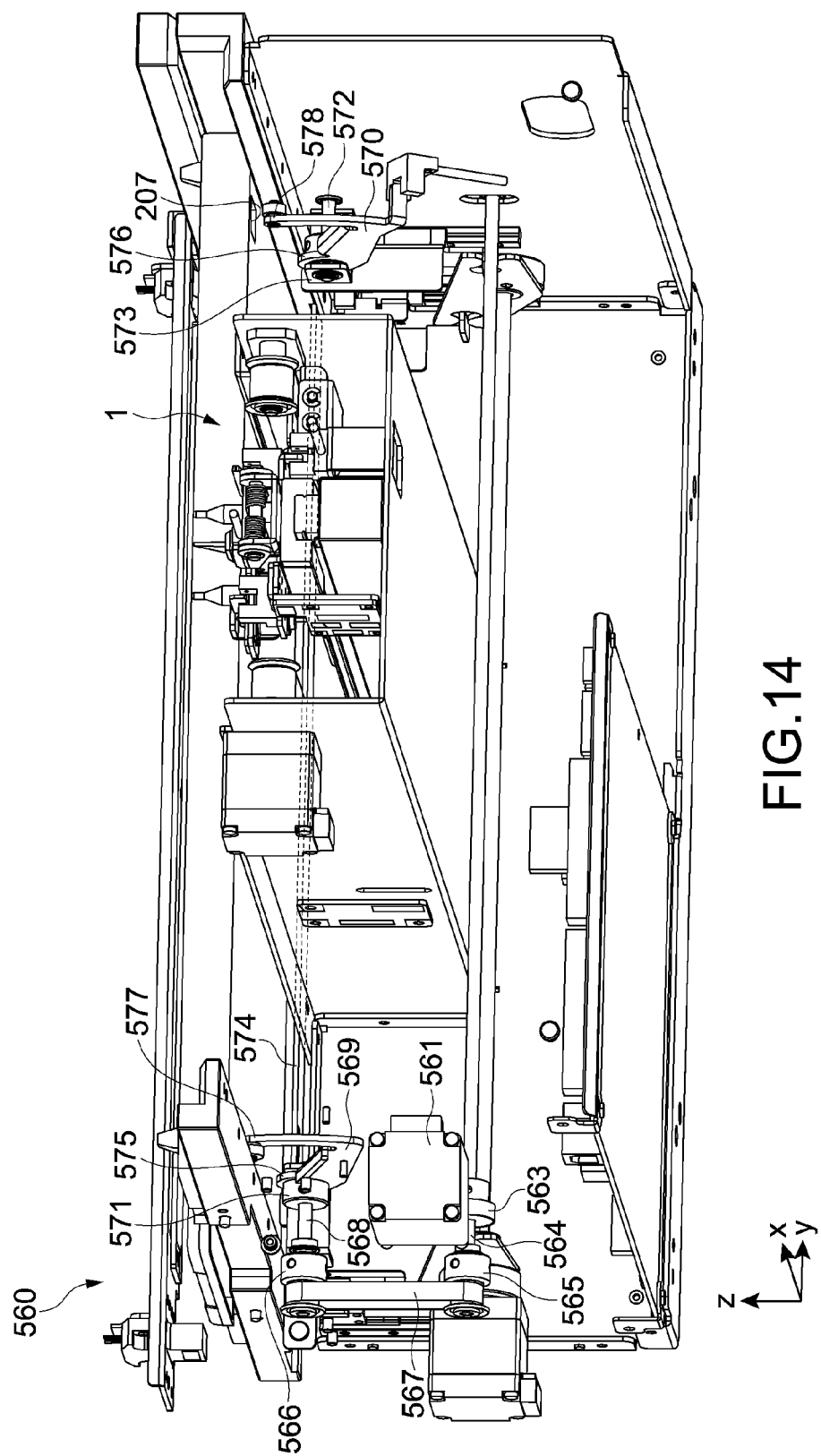
FIG. 14 is a schematic diagram showing a lift-up portion.

FIG. 14 is a schematic diagram showing the lift-up portion 560.

The lift-up portion 560 (switch portion) includes a motor portion 561, a drive gear (not shown), a transmission gear 563, a first shaft 564, a first pulley 565, a second pulley 566, a belt 567, a second shaft 568, a first arm 569, a second arm 570, a holding portion 571, a third shaft 572, a stopper 573, and a coupling axis 574.

The motor portion 561 has a built-in motor (not shown). The motor is rotatable in both directions. A drive gear (not shown) is provided in the motor portion 561. The drive gear is coaxial with a motor shaft (not shown) and outputs power of the motor. The drive gear engages with the transmission gear 563. On the shaft of the transmission gear 563 (first shaft 564), the first pulley 565 is provided coaxial with the transmission gear 563. The transmission gear 563 transmits power transmitted from the drive gear to the first pulley 565 rotating in sync with the transmission gear 563. The belt 567 is wound at an appropriate tension around the first pulley 565 and the second pulley 566 apart from the first pulley 565 in at least the Z direction. With this structure, the second pulley 566 rotates in sync with the first pulley 565. The power transmitted to the first pulley 565 is transmitted to the second pulley 566 by the belt 567. Fixed to the shaft of the second pulley 566 (second shaft 568) is the first arm 569. Specifically, the holding portion 571 is fixed to a first end portion 575 of the first arm 569. The holding portion 571 is a member for holding the first arm 569 while not allowing it to rotate with respect to the second shaft 568. By fixing the holding portion 571 to the second shaft 568, the first arm 569 is fixed to the second shaft 568. As a result, the first arm 569 rotates in sync with the second pulley 566 about the second shaft 568. The first arm 569 is formed at/in such a position and shape that it can penetrate one of the second through-holes 207 of the frame 200 along with the rotation.

The third shaft 572 is coaxial with the second shaft 568. The second arm 570 is provided to the third shaft 572. Specifically, a shaft hole is provided on the second arm 570. The third shaft 572 is inserted into the shaft hole of the second arm 570. The third shaft 572 rotatably supports the second arm 570. At a tip end of the third shaft 572, the stopper 573 is provided. The stopper 573 restricts the second arm 570 from breaking away from the third shaft 572. With this structure, the second arm 570 rotates about the third shaft 572. The second arm 570 is formed at/in such a position and shape that it can penetrate the other second through-hole 207 of the frame 200 along with the rotation.

The coupling axis 574 couples the first end portion 575 of the first arm 569 and a first end portion 576 of the second arm 570. The coupling axis 574 is non-coaxial (decentering) with the second shaft 568 and the third shaft 572. Specifically, the coupling axis 574 couples the first arm 569 and the second arm 570 such that a second end portion 577 of the first arm 569 and a second end portion 578 of the second arm 570 oppose each other in the rotation axis direction (Y direction).

As the first arm 569 rotates about the second shaft 568, the coupling axis 574 provided in the first arm 569 while being non-coaxial with the second shaft 568 rotates about the second shaft 568. At the same time, the second arm 570 coupled to the coupling axis 574 also rotates about the third shaft 572 coaxial with the second shaft 568. With this structure, the first arm 569 and the second arm 570 rotate in sync between a home position and an upper position.

4.2.1.1. First and Second Arms

Figure 15:
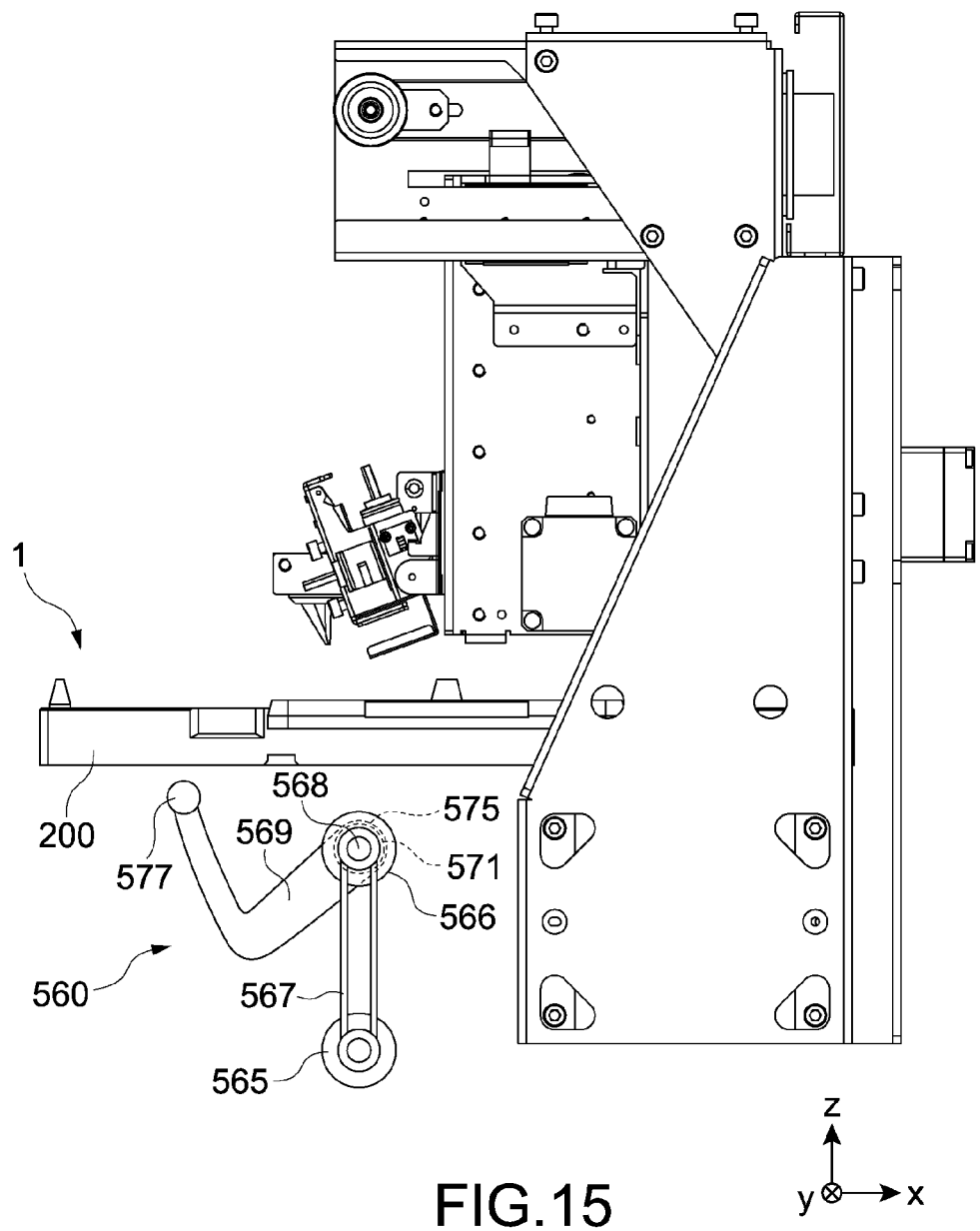
FIG. 15 is a schematic diagram showing the vicinity of a first arm of the lift-up portion in a state where the first arm is in a home position.
Figure 16:
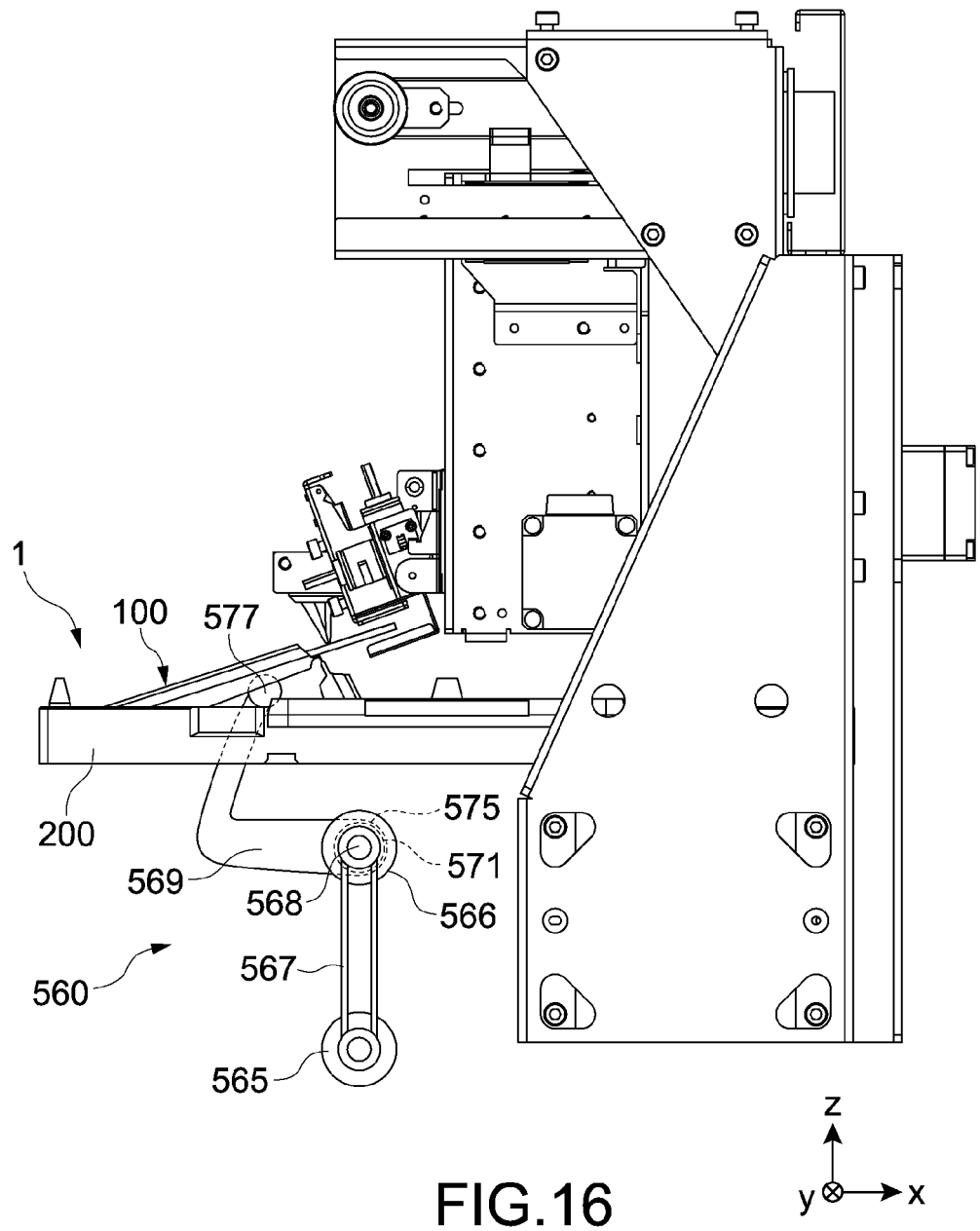
FIG. 16 is a schematic diagram showing the vicinity of the first arm of the lift-up portion in a state where the first arm is in an upper position.

FIG. 15 is a schematic diagram showing the vicinity of the first arm 569 of the lift-up portion 560 in a state where the first arm 569 is at the home position. FIG. 16 is a schematic diagram showing the vicinity of the first arm 569 of the lift-up portion 560 in a state where the first arm 569 is at the upper position.

When the first arm 569 is at the home position (see FIG. 15), the slide accommodation portion 100 of the slide tray 1 is non-tilted. When the first arm 569 is at the upper position (see FIG. 16), the slide accommodation portion 100 of the slide tray 1 is tilted.

Descriptions will be given on the movements of the first arm 569 and second arm 570 of the lift-up portion 560 and the slide tray 1 at a time the slide accommodation portion 100 changes from the home position (slide accommodation portion 100 is in non-tilted state) to the upper position (slide accommodation portion 100 is in tilted state).

When the first arm 569 at the home position is driven by the motor portion 561, the first arm 569 rotates in one direction (direction in which second end portion 577 of first arm 569 is raised) about the second shaft 568. At the same time, the second arm 570 also rotates in sync with the first arm 569 about the third shaft 572. The second end portion 577 of the first arm 569 and the second end portion 578 of the second arm 570 come into contact with the lower surface of the second mount plate 109 and lift up the second mount plate 109 in at least the Z direction while sliding on the lower surface of the second mount plate 109. When the second mount plate 109 is lifted up, the ribs 110 are bent so that the first mount plate 108 and the second mount plate 109 are bent relatively so as to form an angle on the lower surface side. The lift-up portion 560 is designed such that the rotation of the first arm 569 stops when the first arm 569 rotates a predetermined angle. When the rotation of the first arm 569 stops, the rotation of the second arm 570 also stops in sync with the first arm 569, and the first arm 569 and the second arm 570 are at the upper position, the slide accommodation portion 100 is positioned in the tilted state.

It should be noted that the lift-up portion 560 only needs to be designed such that, when the slide accommodation portion 100 is positioned in the tilted state, an angle between the setup plate 201 of the frame 200 and the second mount plate 109 of the slide accommodation portion 100 becomes, for example, about 18 degrees. About 18 degrees is considered to be a value with which the grip portion 530 can easily stick a lower jaw 532 thereof between the slide mounted on the second mount plate 109 and the first mount plate 108 to thus grip and take out the slide using an upper jaw and the lower jaw 532.

Descriptions will be given on the movements of the first arm 569 and second arm 570 of the lift-up portion 560 and the slide tray 1 at a time the slide accommodation portion 100 changes from the upper position (slide accommodation portion 100 is in tilted state) to the home position (slide accommodation portion 100 is in non-tilted state).

When the first arm 569 at the upper position is driven by the motor, the first arm 569 rotates in the opposite direction (direction in which second end portion 577 of first arm 569 is lowered) about the second shaft 568. At the same time, the second arm 570 also rotates in sync with the first arm 569 about the third shaft 572. As the second end portion 577 of the first arm 569 and the second end portion 578 of the second arm 570 are lowered, the second mount plate 109 lifted up by the second end portion 577 of the first arm 569 and the second end portion 578 of the second arm 570 is also lowered. With this structure, the bent ribs 110 of the slide accommodation portion 100 become flat again, and thus the first mount plate 108 and the second mount plate 109 that have been bent relatively also become flat again. The lift-up portion 560 is designed such that, when the second end portion 577 of the first arm 569 and the second end portion 578 of the second arm 570 reach positions opposing the lower surface of the flat second mount plate 109 in a contact or non-contact state, the rotation of the first arm 569 stops, and the rotation of the second arm 570 also stops in sync with the first arm 569 so that the first arm 569 and the second arm 570 come to the home position. As a result, the slide accommodation portion 100 is positioned in the non-tilted state.

4.2.2. Grip Portion

Figure 17:
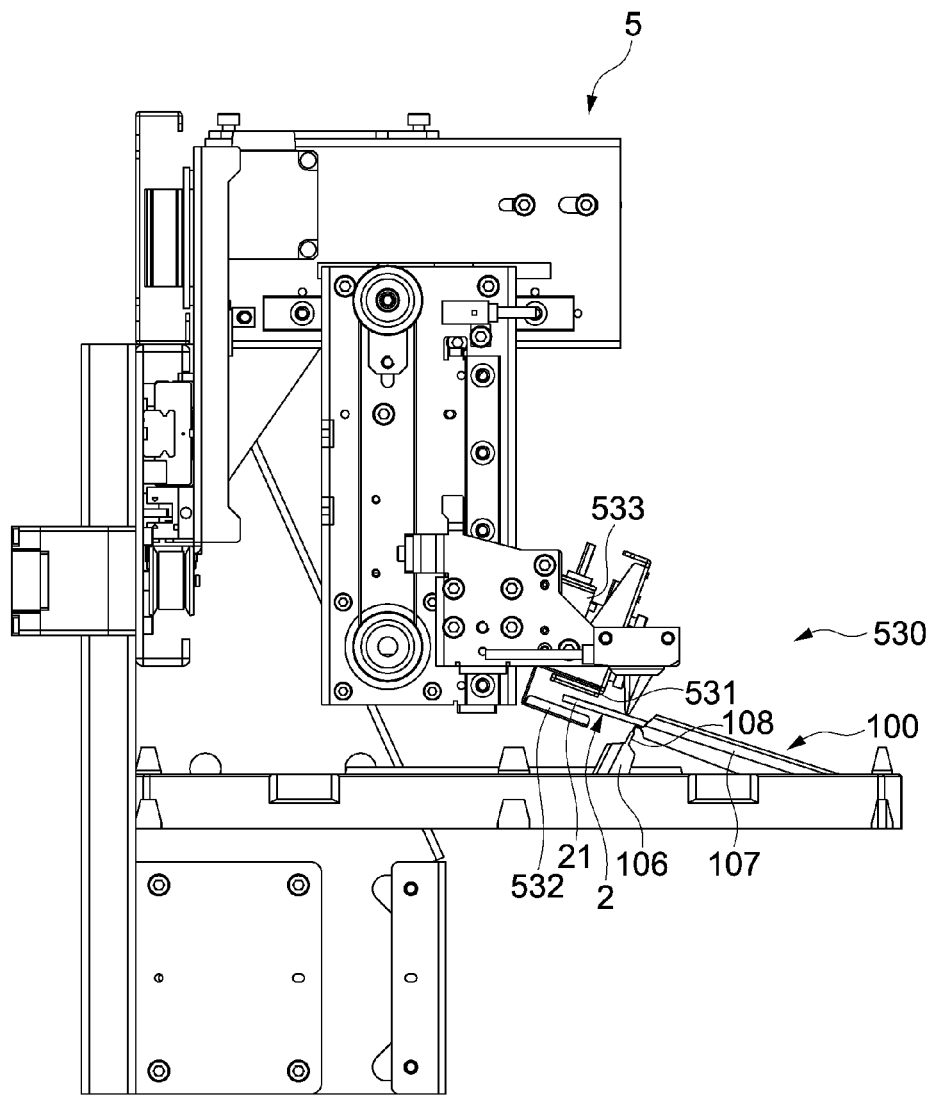
FIG. 17 is a side view of a grip portion.

FIG. 17 is a side view of the grip portion 530.

The grip portion 530 includes the upper jaw 531, the lower jaw 532, and a drive portion 533. The drive portion 533 drives the upper jaw 531 and the lower jaw 532 as follows.

When the slide accommodation portion 100 is in the tilted state, the slide 2 is released from the first accommodation portion 106 and accommodated only in the second accommodation portion 107. One end portion of the slide mounted on the first mount plate 108 is not in contact with the first mount plate 108 and is floating from the first mount plate 108. The lower jaw 532 enters between one end portion 21 of the slide 2 and the first mount plate 108 and opposes a back surface of the one end portion 21 of the slide 2 in the Z direction. The lower jaw 532 is tilted at almost the same angle as the tilt angle of the second mount plate 109 (specifically, as tilt angle of slide 2). The upper jaw 531 opposes a front surface of the one end portion 21 of the slide 2 in the Z direction and opposes the lower jaw 532 in the Z direction via the one end portion 21 of the slide 2. The lower jaw 532 comes into contact with the back surface of the one end portion 21 of the slide 2, and the upper jaw 531 comes into contact with the front surface of the slide 2. As a result, the upper jaw 531 and the lower jaw 532 grip the slide 2 accommodated in the slide tray 1 in the Z direction.

4.2.3. Conveyor Portion

Figure 18:
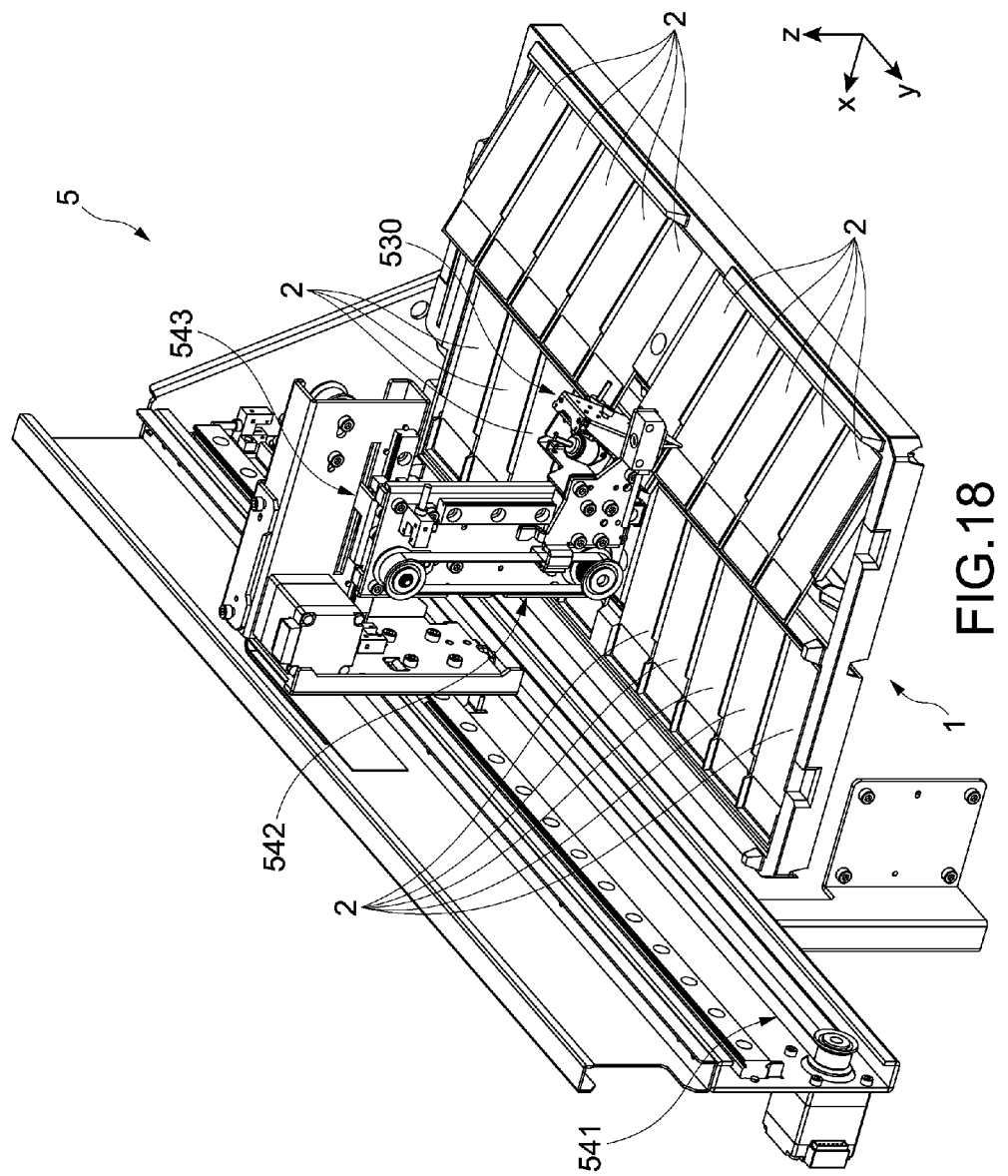
FIG. 18 is a perspective view of a conveyor portion.

FIG. 18 is a perspective view of the conveyor portion 540.

The conveyor portion 540 includes a Y-direction conveyor portion 541, a Z-direction conveyor portion 542, and an X-direction conveyor portion 543.

Before the grip portion 530 grips the slide 2, the Y-direction conveyor portion 541 conveys the grip portion 530 in the Y direction to position the grip portion 530 in the Y direction with respect to the slide 2 to be gripped. The Z-direction conveyor portion 542 conveys the grip portion 530 in the Z direction to position the grip portion 530 in the Z direction with respect to the slide to be gripped. The X-direction conveyor portion 543 conveys the grip portion 530 in the X direction so that the upper jaw 531 and lower jaw 532 of the grip portion 530 oppose the one end portion of the slide 2 in the Z direction while sandwiching it.

After the grip portion 530 grips the slide 2, the X-direction conveyor portion 543 conveys the grip portion 530 in the X direction and hands over the grip portion 530 to the Z-direction conveyor portion 542. The Z-direction conveyor portion 542 conveys the grip portion 530 in the Z direction and hands over the grip portion 530 to the Y-direction conveyor portion 541. The Y-direction conveyor portion 541 conveys the grip portion 530 in the Y direction and hands over the grip portion 530 to the scanner portion 550 (see FIG. 13) provided in the vicinity of a Y-direction end portion of the Y-direction conveyor portion 541.

5. Effect

According to this embodiment, it becomes possible to easily take out the slide 2 manually from the slide tray 1 without enlarging the overall slide tray 1. Specifically, when the slide accommodation portion 100 is in the tilted state, the first mount plate 108 and the second mount plate 109 are also tilted. The X-direction length of the second mount plate 109 is larger than that of the first mount plate 108. Therefore, the slide 2 is released from the first mount plate 108 and mounted only on the second mount plate 109. The one end portion 21 of the slide 2 mounted on the first mount plate 108 is released from the first mount plate 108 and floats from the first mount plate 108. With this structure, the user can insert a finger between the one end portion 21 of the slide 2 and the first mount plate 108 and pinch the upper and lower surfaces of the slide 2 to easily take it out.

Further, according to this embodiment, it is possible to accommodate the stacked slide trays 1 in the slide conveyor apparatus 5 so that the slide conveyor apparatus 5 can easily take out the slide 2 accommodated in the slide trays 1. Therefore, the task of manually moving the slide 2 accommodated in the slide tray 1 having fine visibility to a dedicated cassette can be eliminated. Specifically, when the slide accommodation portion 100 is in the tilted state, the grip portion 530 of the slide conveyor apparatus 5 can insert the lower jaw 532 between the one end portion 21 of the slide 2 and the first mount plate 108 and easily grip and take out the slide using the upper jaw 531 and the lower jaw 532.

Furthermore, since the second mount plate 109 is tilted when the slide accommodation portion 100 is in the tilted state, the other end portion of the slide 2 comes into contact with the second outer frame 105 of the slide accommodation portion 100. With this structure, the other end portions of one or more slides are aligned in the Y direction while being in contact with the second outer frames 105. As a result, the one end portions 21 of the one or more slides 2 are also aligned in the Y direction. In other words, the protrusion lengths of the one or more slides 2 in the X direction become the same. Therefore, it becomes unnecessary to adjust the position of the grip portion 530 of the slide conveyor apparatus 5 in the X direction every time the grip portion 530 grips the one or more slides 2. Consequently, the grip portion 530 can easily and positively grip the one or more slides 2.

Modified Example 1

Hereinafter, structures and the like that are the same as those described above are denoted by the same reference numerals. Moreover, descriptions on structures, moves, functions, and the like that are the same as those described above will be omitted or simplified, and different points will mainly be described.

Figure 19:
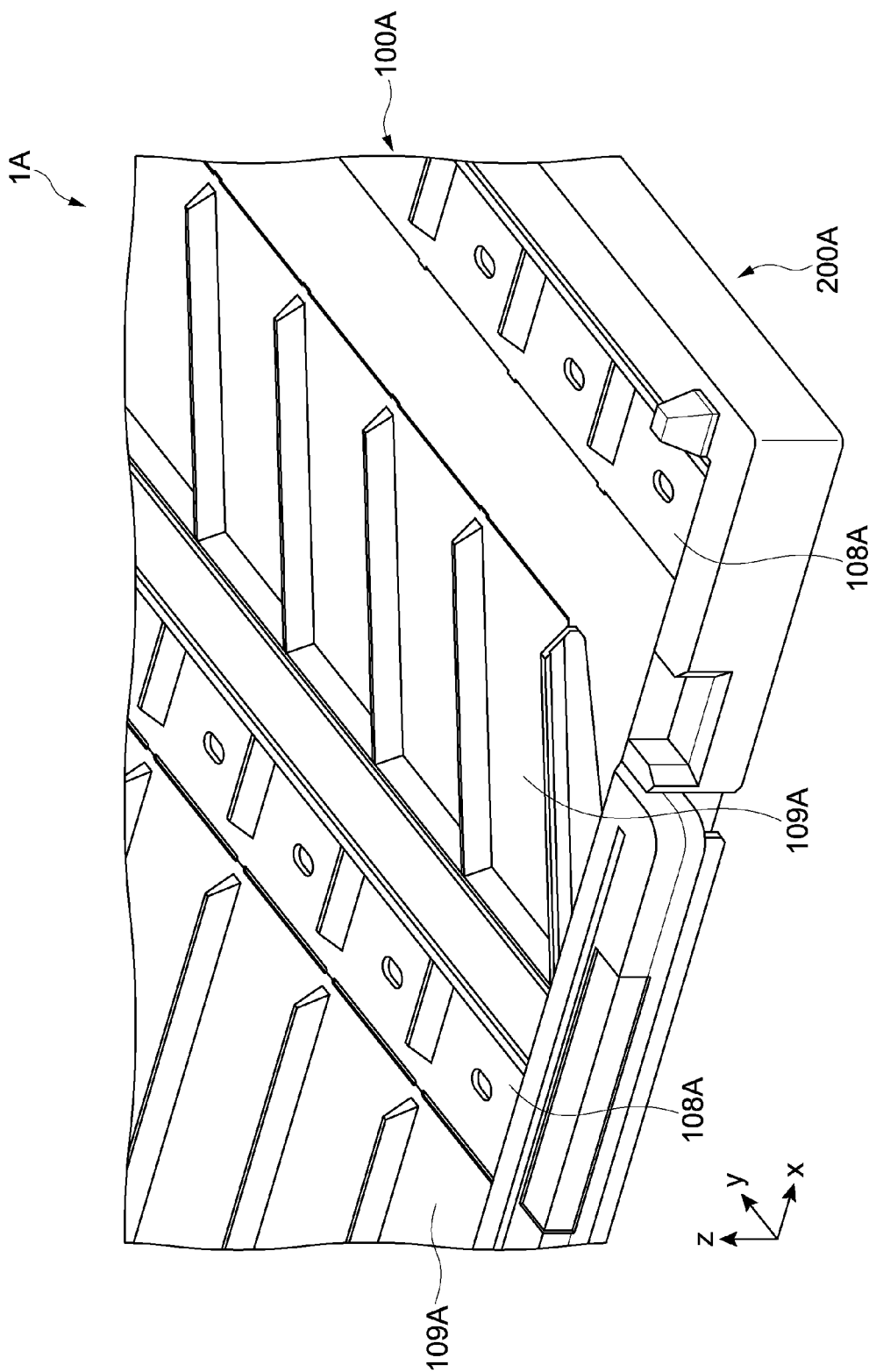
FIG. 19 is a perspective view partially showing a slide tray according to Modified Example 1.

FIG. 19 is a perspective view partially showing a slide tray according to Modified Example 1.

In the embodiment above, the first mount plate 108 and second mount plate 109 of the slide accommodation portion 100 are separated and connected at least partially by one or more ribs 110. By bending the rib 110, the first mount plate 108 and the second mount plate 109 have been relatively bent. In contrast, in a slide tray 1A according to Modified Example 1, the ribs 110 that partially connect the first mount plate 108 and the second mount plate 109 are not provided, and a first mount plate 108A and a second mount plate 109A are totally separated. When a slide accommodation portion 100A is in a tilted state, the second mount plate 109A is tilted as in the embodiment above. On the other hand, the position of the first mount plate 108A does not change between the non-tilted state and the tilted state. Therefore, the first boss 122 and the long hole 210 that have guided the tilt of the first mount plate 108 in the embodiment above are unnecessary in a frame 200A of Modified Example 1.

Also in this example, it is possible to make a switch between the non-tilted state where an entire surface of one or more slides is mounted on the slide accommodation portion 100A and the tilted state where one end portion of the one or more slides is released from the slide accommodation portion 100A. Modified Example 1 bears the same effect as the embodiment above.

Modified Example 2

In the embodiment above, the flip-up portion 300 has been provided as a mechanism for manually switching the slide accommodation portion 100 between the tilted state and the non-tilted state. In contrast, in Modified Example 2, another mechanism (slide lever mechanism) is provided as the mechanism for manually making a switch between the tilted state and the non-tilted state.

1. Structure of Slide Tray

Figure 20:
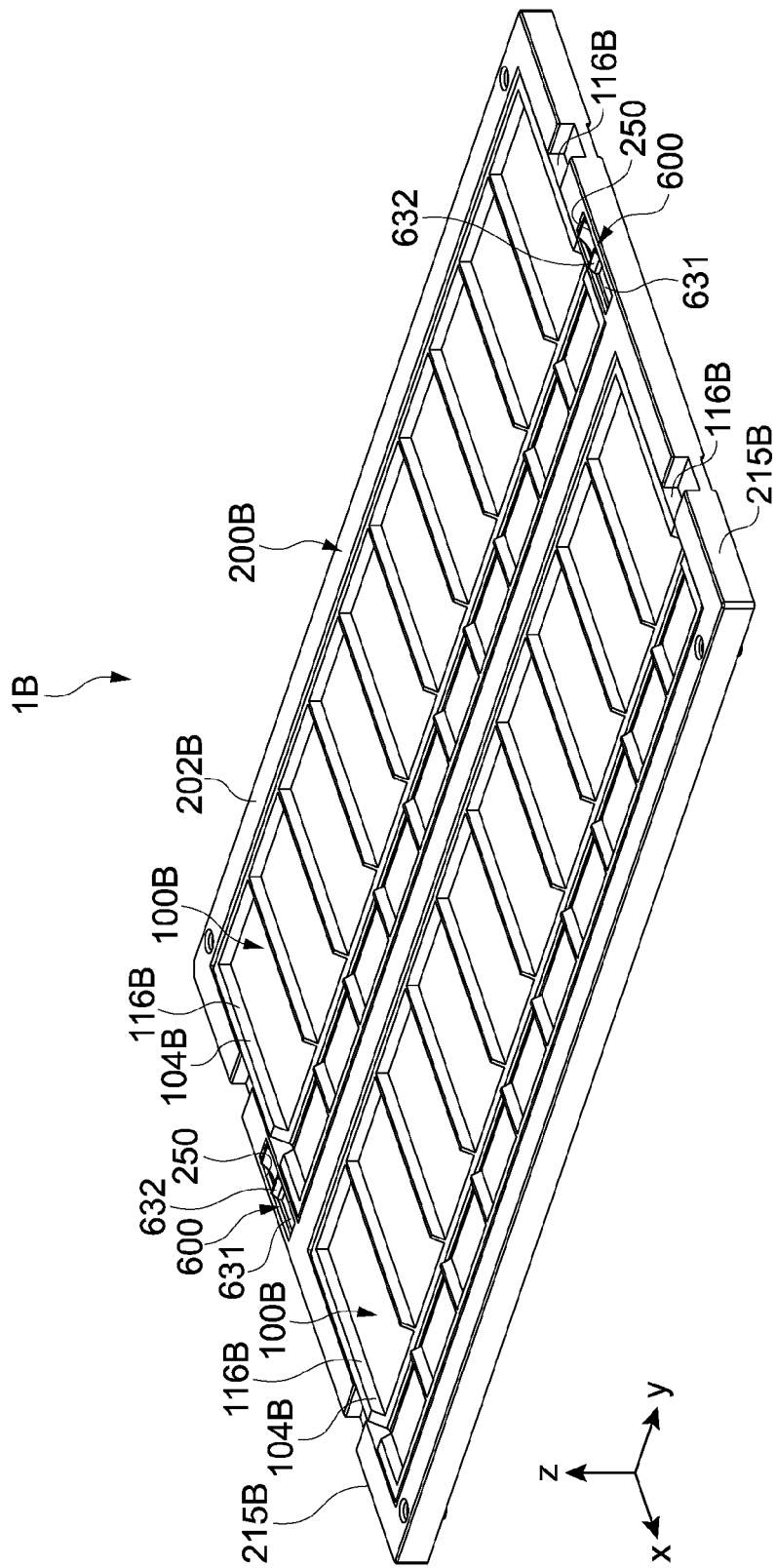
FIG. 20 is a perspective view of a slide tray according to Modified Example 2.
Figure 21:
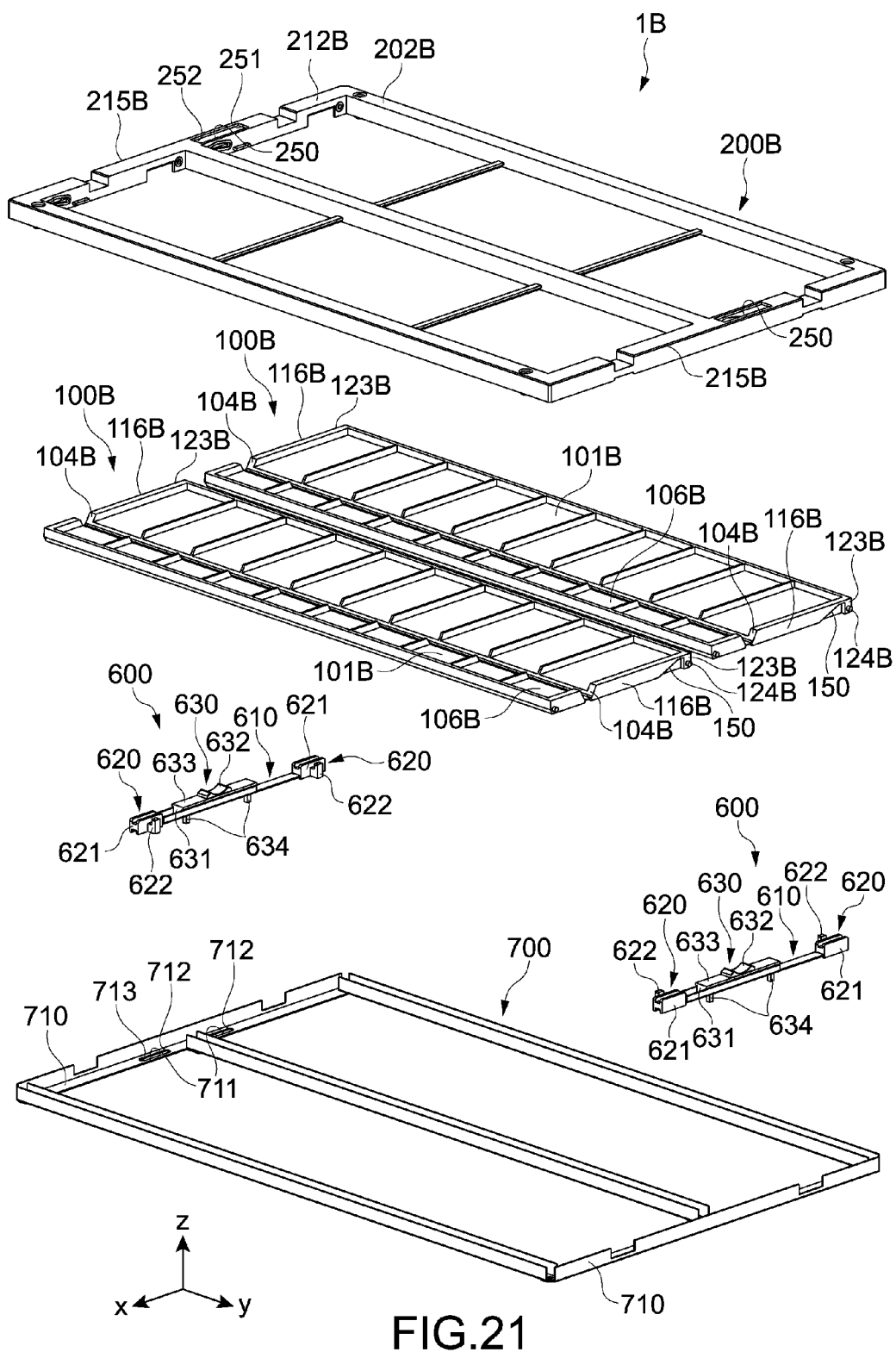
FIG. 21 is an exploded perspective view of the slide tray according to Modified Example 2.

FIG. 20 is a perspective view of a slide tray 1B according to Modified Example 2. FIG. 21 is an exploded perspective view of the slide tray 1B according to Modified Example 2.

The slide tray 1B includes a pair of slide levers 600, a lower frame 700, an upper frame 200B, and one or more slide accommodation portions 100B. It should be noted that herein, the two slide accommodation portions 100B are provided in the slide tray 1B.

1.1. Structure of Slide Lever

The pair of slide levers 600 have the same shape. Therefore, descriptions below will be given on one of the slide levers 600. The slide lever 600 includes a base 610, two engagement portions 620, and a lever portion 630.

The base 610 is elongated in the X direction and accommodated in a frame outer frame 202B of the upper frame 200B along a third side 215B of the upper frame 200B. Fixed to the base 610 are the two engagement portions 620 and the lever portion 630. A positional relationship between the two engagement portions 620 and the lever portion 630 fixed to the base 610 is as follows.

The two engagement portions 620 have the same shape. Therefore, descriptions below will be given on one of the engagement portions 620. The engagement portion 620 includes a slide portion 621 and an engagement piece 622. The slide portion 621 of one of the engagement portions 620 comes into contact with a second frame portion 116B of one of the slide accommodation portions 100B while surfaces thereof oppose each other. The slide portion 621 of the other one of the engagement portions 620 comes into contact with the second frame portion 116B of the other one of the slide accommodation portions 100B while surfaces thereof oppose each other. The engagement piece 622 protrudes from the slide portion 621 in at least the Y direction. A distance between centers of the two engagement pieces 622 is the same as that between centers of the one or more slide accommodation portions 100B.

The lever portion 630 includes a lever base 631 and a tab 632. The lever base 631 protrudes from the base 610 in the Z direction and is elongated in the X direction. The tab 632 is provided on an upper surface 633 of the lever base 631 and protrudes in the Z direction. On a lower surface of the lever base 631, one or more stopper protrusions 634 are provided. The one or more stopper protrusions 634 penetrate through-holes (not shown) provided on the base 610 and protrude from the lower surface of the base 610 in the Z direction. In this example, two stopper protrusions 634 are provided.

1.2. Structure of Lower Frame 700

The lower frame 700 is fixed to the lower surface of the upper frame 200B. The slide levers are set on a pair of frame portions 710 of the lower frame 700 that extend in the X direction. The pair of frame portions 710 have the same shape. Therefore, descriptions below will be given on one of the frame portions 710. On a bottom surface of the frame portion 710, one or more long holes 711 penetrating in the Z direction are formed. The number of long holes 711 is the same as the number of stopper protrusions 634 of the slide lever 600. In this example, two long holes 711 are formed. The X-direction length of the two long holes 711 are the same. A distance between centers of the two long holes 711 is the same as that between centers of the two stopper protrusions 634. The two stopper protrusions 634 are respectively inserted into the two long holes 711. The two stopper protrusions 634 are slidable in the two long holes 711 in the X direction. Both end portions of the two long holes 711 in the X direction restrict the two stopper protrusions 634 from moving in the X direction. With this structure, the slide lever 600 can reciprocate a predetermined distance in the X direction.

1.3. Structure of Upper Frame 200B

Points different from those of the frame 200 of the embodiment above will be described. A pair of third through-holes 250 are provided on an upper surface 212B of the frame outer frame 202B. The pair of third through-holes 250 have the same structure. Therefore, descriptions below will be given on one of the third through-holes 250. The third through-hole 250 penetrates the frame outer frame 202B in the Z direction. The third through-hole 250 is provided along a third side 215B and elongated in the X direction. The X-direction length of the third through-hole 250 is equal to or larger than that of the long holes 711 of the lower frame 700. The tab 632 of the slide lever 600 set on the lower frame 700 protrudes from the third through-hole 250 in the Z direction. The X-direction length of the lever base 631 of the slide lever 600 is larger than that of the third through-hole 250. Therefore, a part of the upper surface 203 of the slide lever base 631 comes into contact with the frame outer frame 202B, thus restricting the entire lever base 631 from breaking off from the third through-hole 250 in the Z direction. With this structure, the user can cause the tab 632 protruding from the third through-hole 250 to reciprocate in the X direction.

1.4. Structure of Slide Accommodation Portion 100B

A third notch 150 is formed on a first outer frame 104B of the slide accommodation portion 100B at a position close to a fourth end portion 123B of the second frame portion 116B. More specifically, the third notch 150 is formed at a position that does not interfere with a second boss 124B provided at the fourth end portion 123B. The third notch 150 has such a tapered shape that a distance from an upper surface of a mount plate 101B gradually increases (notch becomes deeper) as a distance from a first accommodation portion 106B increases in the X direction. More specifically, the third notch 150 is formed as follows.

Figure 22:
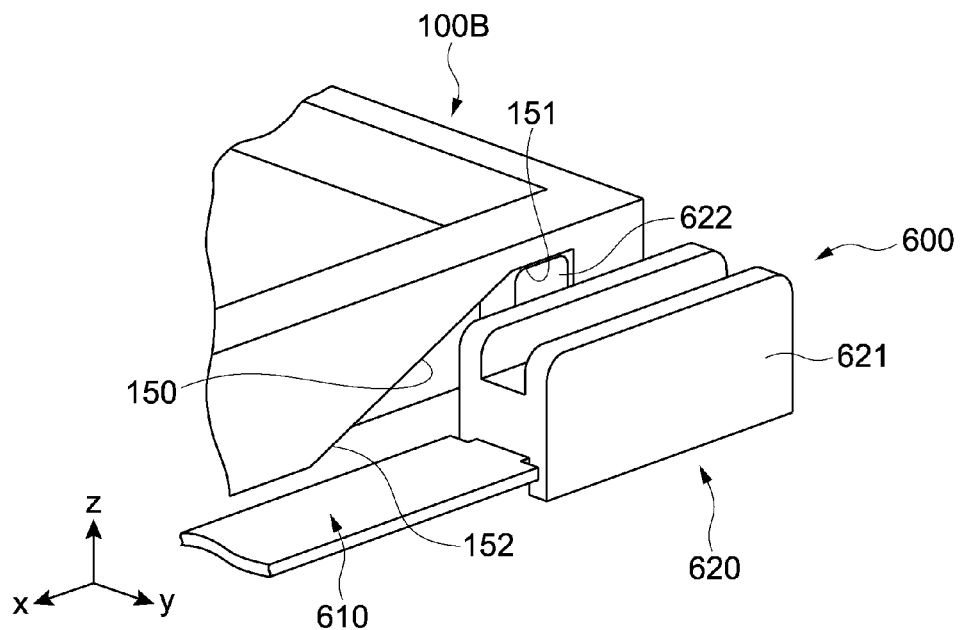
FIG. 22 is a perspective view showing a shape of a third notch and a positional relationship between the third notch and an engagement piece.

FIG. 22 is a perspective view showing the shape of the third notch 150 and a positional relationship between the third notch 150 and the engagement piece 622.

It is assumed that the stopper protrusions 634 of the slide lever 600 are in contact with first end portions 712 (end portions distant from first accommodation portion 106 in X direction, see FIG. 21) of the long holes 711 of the lower frame 700. At this time, the engagement piece 622 of the slide lever 600 opposes a deep-notch (specifically, depth of notch is equal to or larger than Z-direction height of engagement piece 622) portion 151 of the third notch 150. Therefore, the engagement piece 622 is fully accommodated in the third notch 150.

Figure 23:
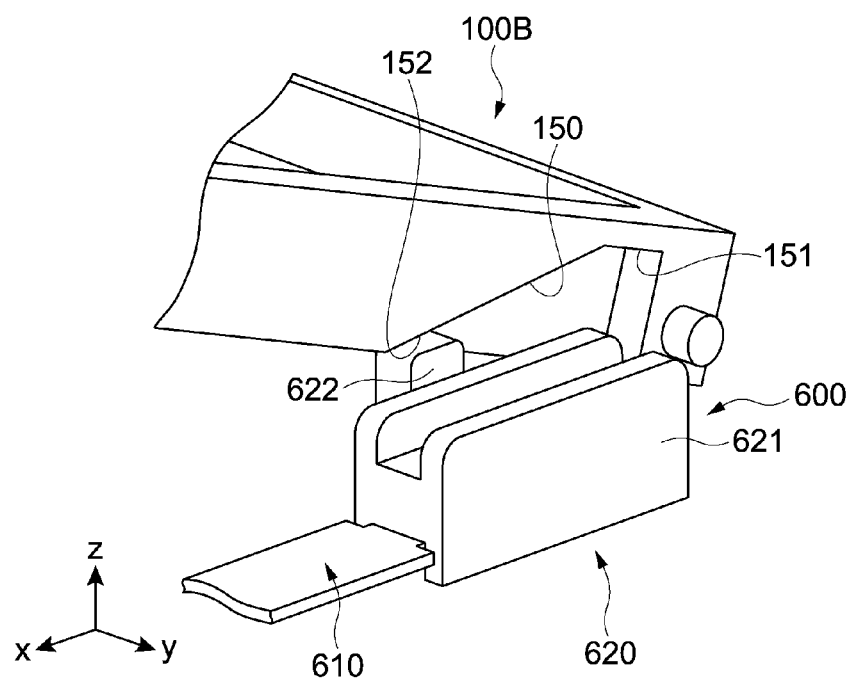
FIG. 23 is a perspective view showing the shape of the third notch and another positional relationship between the third notch and the engagement piece.

FIG. 23 is a perspective view showing the shape of the third notch 150 and another positional relationship between the third notch 150 and the engagement piece 622.

On the other hand, it is assumed that the stopper protrusions 634 come into contact with second end portions 713 (end portions closer to first accommodation portion 106 in X direction, see FIG. 21) of the long holes 711. At this time, the engagement piece 622 opposes a shallow-notch (specifically, depth of notch is smaller than Z-direction height of engagement piece 622) portion 152 of the third notch 150, that has a smaller depth than the engagement piece 622. Therefore, at least a part of the engagement piece 622 cannot enter the third notch 150, and thus the third notch 150 is lifted up.

Figure 24:
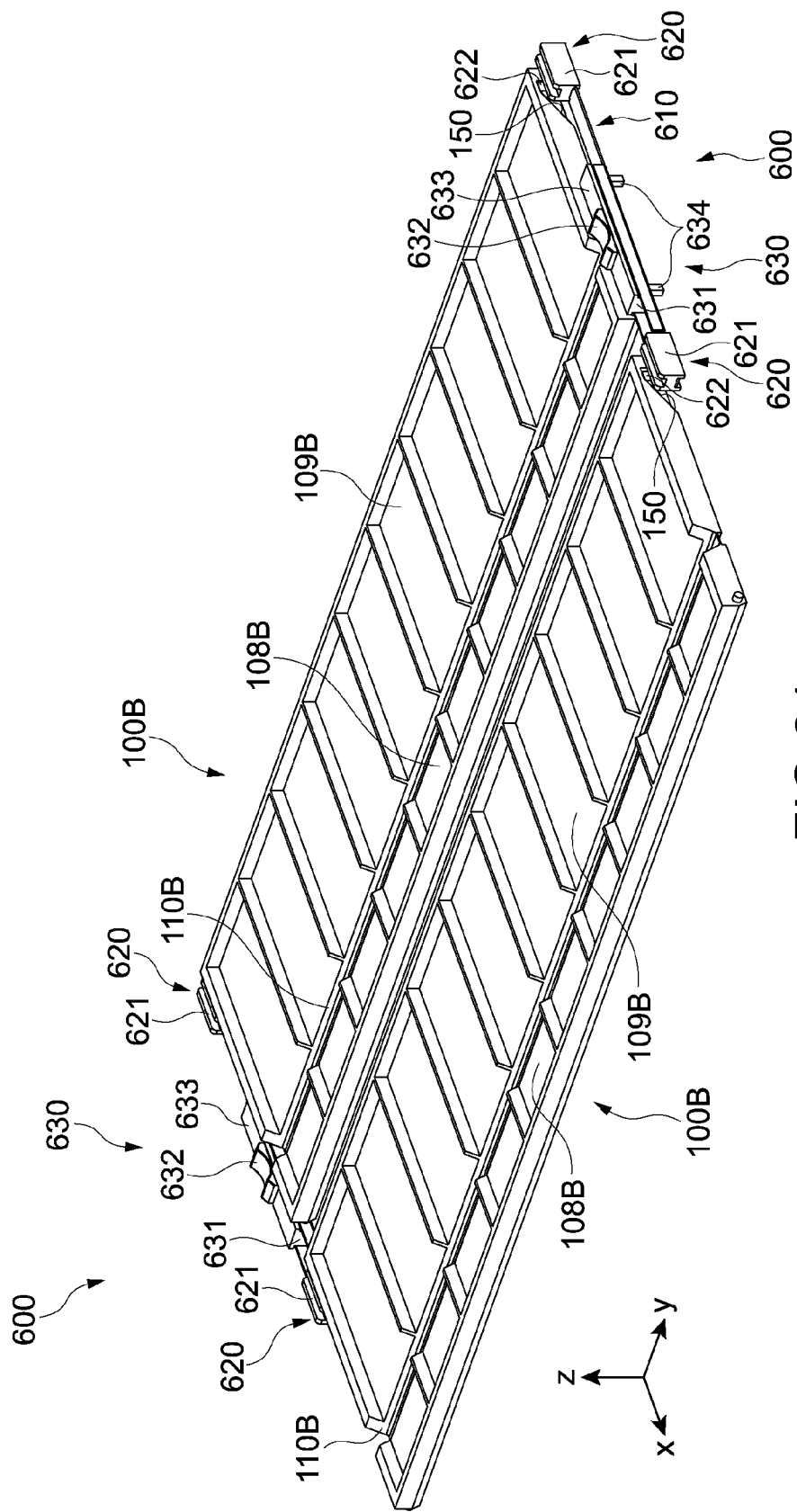
FIG. 24 is a schematic diagram showing two non-tilted accommodation portions and slide levers.
Figure 25:
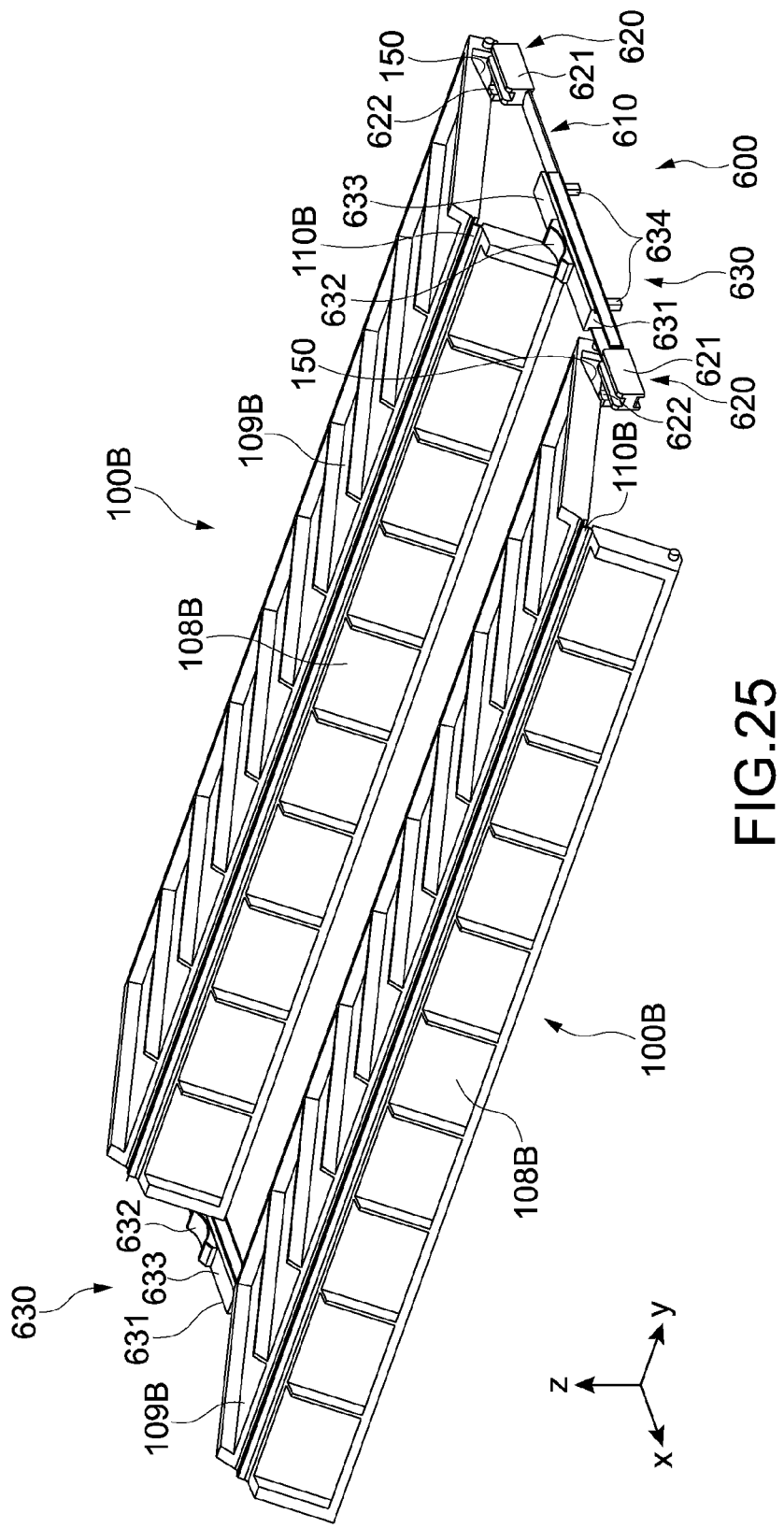
FIG. 25 is a schematic diagram showing two tilted accommodation portions and the slide levers.

2. Moves of Slide Tray 1B 2.1. Moves of Slide Tray 1B at Time it Changes from Non-Tilted State to Tilted State FIG. 24 is a schematic diagram showing two non-tilted accommodation portions 100B and the slide levers 600. FIG. 25 is a schematic diagram showing two tilted accommodation portions 100B and the slide levers 600.

When the slide accommodation portion 100B is in the non-tilted state, the stopper protrusions 634 of the slide lever 600 are in contact with the first end portions 712 (see FIG. 21) of the long holes 711 of the lower frame 700. The tab 632 of the slide lever comes near or in contact with a first end portion 251 (end portion distant from first accommodation portion 106 in X direction) of the third through-hole 250 of the upper frame 200B. The engagement piece 622 of the slide lever 600 is fully accommodated in the third notch 150. When a pressing force in the X direction (direction that approaches first accommodation portion 106) is imparted to the tab 632 by a finger of the user or the like, the stopper protrusions 634 move in the X direction in the long holes 711. The engagement piece 622 moves in a direction in which the depth of the notch becomes smaller in the third notch 150. At this time, a tip end portion of the engagement piece 622 lifts up the second mount plate 109B in the Z direction while sliding in the third notch 150. As the second mount plate 109B is lifted up, the ribs 110B are bent so that the first mount plate 108B and the second mount plate 109B are relatively bent so as to form an angle on the lower surface side. As the stopper protrusions 634 come into contact with the second end portions 713 (see FIG. 21) of the long holes 711, the slide lever 600 is restricted from moving further in the X direction. As a result, the slide accommodation portion 100B is positioned in the tilted state.

2.2. Moves of Slide Tray 1B at Time it Changes from Tilted State to Non-tilted State When the slide accommodation portion 100B is in the tilted state, the stopper protrusions 634 of the slide lever 600 are in contact with the second end portions 713 (see FIG. 21) of the long holes 711 of the lower frame 700. The tab 632 of the slide lever 600 comes near or in contact with a second end portion 252 (end portion closer to first accommodation portion 106 in X direction) of the third through-hole 250 of the upper frame 200B. The engagement piece 622 of the slide lever 600 lifts up the third notch 150. When a pressing force in the X direction (direction that moves farther away from first accommodation portion 106) is imparted to the tab 632 by a finger of the user or the like, the stopper protrusions 634 move in the X direction in the long holes 711. The engagement piece 622 moves in a direction in which the depth of the notch becomes larger in the third notch 150. At this time, the engagement piece 622 gradually goes deeper into the third notch 150. As a result, the second mount plate 109B lifted up by the engagement piece 622 is lowered. Accordingly, the bent ribs 110B of the slide accommodation portion 100B become flat, and thus the first mount plate 108B and the second mount plate 109B that have been relatively bent also become flat. As the stopper protrusions 634 come into contact with the first end portions 712 (see FIG. 21) of the long holes 711, the slide lever 600 is restricted from moving any further in the X direction. Consequently, the slide accommodation portion 100B is positioned in the non-tilted state.

Also in this example, a switch can be made between the non-tilted state where an entire surface of one or more slides is mounted on the slide accommodation portion 100B and the tilted state where one end portion of the one or more slides is released from the slide accommodation portion 100B. This example bears the same effect as the embodiment above.

Others

It should be noted that the present disclosure may also take the following structures.

(1) A slide tray, including:
a slide accommodation portion capable of accommodating one or more slides mounted thereon; and
a switch portion that makes a switch between a first state in which an entire surface of the one or more slides is mounted on the slide accommodation portion and a second state in which one end portion of the one or more slides is released from the slide accommodation portion.

(2) The slide tray according to (1) above,
in which a mount position of the one or more slides in the second state is tilted a predetermined angle with respect to a mount position of the one or more slides in the first state.

(3) The slide tray according to (1) or (2) above,
in which the slide accommodation portion includes
a first accommodation portion that accommodates the one end portion of the one or more slides, and
a second accommodation portion that accommodates a part of the one or more slides excluding the one end portion, the second accommodation portion being spatially apart from the first accommodation portion, and
in which the switch portion makes a switch from the first state to the second state by tilting the second accommodation portion.

(4) The slide tray according to any one of (1) to (3) above,
in which the switch portion makes a switch from the first state to the second state by tilting the second accommodation portion using one end portion of the second accommodation portion distant from the first accommodation portion as a fulcrum.

(5) The slide tray according to any one of (1) to (4) above,
in which the switch portion tilts the second accommodation portion using the one end portion of the second accommodation portion as a fulcrum by lifting the second accommodation portion from below.

(6) The slide tray according to any one of (1) to (5) above, further including:
a frame that accommodates the slide accommodation portion; and
a first support portion that rotatably supports the one end portion of the second accommodation portion with respect to the frame,
in which the switch portion makes a switch from the first state to the second state by tilting the second accommodation portion using the first support portion as a fulcrum.

(7) The slide tray according to any one of (1) to (6) above, further including:
a connection portion that relatively and bendably connects the first accommodation portion and the second accommodation portion; and
a second support portion that rotatably supports one end portion of the first accommodation portion distant from the second accommodation portion with respect to the frame and supports the one end portion of the first accommodation portion such that the one end portion is movable in a direction in which the first accommodation portion and the second accommodation portion are adjacent to each other,
in which the switch portion makes a switch from the first state to the second state by tilting the second accommodation portion using the first support portion as a fulcrum and moving the one end portion of the first accommodation portion in an approaching direction with respect to the second accommodation portion.

(8) A slide conveyor apparatus, including:
a switch portion that switches a slide accommodation portion of a slide tray, which is capable of accommodating one or more slides mounted thereon, between a first state in which an entire surface of the one or more slides is mounted on the slide accommodation portion and a second state in which one end portion of the one or more slides is released from the slide accommodation portion;
a grip portion that grips the one end portion of the slide accommodated in the slide accommodation portion switched to the second state; and
a conveyor portion that conveys the slide gripped by the grip portion by moving the grip portion.

(9) The slide conveyor apparatus according to (8) above, in which a mount position of the one or more slides in the second state is tilted a predetermined angle with respect to a mount position of the one or more slides in the first state.

(10) The slide conveyor apparatus according to (8) or (9) above,
in which the slide accommodation portion includes
a first accommodation portion that accommodates the one end portion of the one or more slides, and
a second accommodation portion that accommodates a part of the one or more slides excluding the one end portion, the second accommodation portion being spatially apart from the first accommodation portion, and
in which the switch portion makes a switch from the first state to the second state by tilting the second accommodation portion.

(11) The slide conveyor apparatus according to any one of (8) to (10) above,
in which the switch portion makes a switch from the first state to the second state by tilting the second accommodation portion using one end portion of the second accommodation portion distant from the first accommodation portion as a fulcrum.

(12) The slide conveyor apparatus according to any one of (8) to (11) above,
in which the switch portion tilts the second accommodation portion using the one end portion of the second accommodation portion as a fulcrum by lifting the second accommodation portion from below.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF REFERENCE SYMBOLS 1, 1A, 1B slide tray
2 slide
5 slide conveyor apparatus
100, 100A, 100B slide accommodation portion
200 frame
300 flip-up portion
560 lift-up portion
530 grip portion
540 conveyor portion
550 scanner portion
600 slide lever

The invention claimed is:
1. A slide tray, comprising:
a slide accommodation portion capable of accommodating one or more slides mounted thereon;
a frame that accommodates the slide accommodation portion; and
a switch portion, provided on a lower surface of the frame, that makes a switch between a first state in which an entire surface of the one or more slides is mounted on the slide accommodation portion and a second state in which one end portion of the one or more slides is released from the slide accommodation portion.

2. The slide tray according to claim 1,
wherein a mount position of the one or more slides in the second state is tilted a predetermined angle with respect to a mount position of the one or more slides in the first state.

3. The slide tray according to claim 2,
wherein the slide accommodation portion includes
a first accommodation portion that accommodates the one end portion of the one or more slides, and
a second accommodation portion that accommodates a part of the one or more slides excluding the one end portion, the second accommodation portion being spatially apart from the first accommodation portion, and
wherein the switch portion makes a switch from the first state to the second state by tilting the second accommodation portion.

4. The slide tray according to claim 3,
wherein the switch portion makes a switch from the first state to the second state by tilting the second accommodation portion using one end portion of the second accommodation portion distant from the first accommodation portion as a fulcrum.

5. The slide tray according to claim 4,
wherein the switch portion tilts the second accommodation portion using the one end portion of the second accommodation portion as a fulcrum by lifting the second accommodation portion from below.

6. The slide tray according to claim 5, further comprising:
a first support portion that rotatably supports the one end portion of the second accommodation portion with respect to the frame,
wherein the switch portion makes a switch from the first state to the second state by tilting the second accommodation portion using the first support portion as a fulcrum.

7. The slide tray according to claim 6, further comprising:
a connection portion that relatively and bendably connects the first accommodation portion and the second accommodation portion; and
a second support portion that rotatably supports one end portion of the first accommodation portion distant from the second accommodation portion with respect to the frame and supports the one end portion of the first accommodation portion such that the one end portion is movable in a direction in which the first accommodation portion and the second accommodation portion are adjacent to each other,
wherein the switch portion makes a switch from the first state to the second state by tilting the second accommodation portion using the first support portion as a fulcrum and moving the one end portion of the first accommodation portion in an approaching direction with respect to the second accommodation portion.

8. A slide conveyor apparatus, comprising:
a switch portion that switches a slide accommodation portion of a slide tray, which is capable of accommodating one or more slides mounted thereon, between a first state in which an entire surface of the one or more slides is mounted on the slide accommodation portion and a second state in which one end portion of the one or more slides is released from the slide accommodation portion,
wherein the slide tray comprises a frame that accommodates the slide accommodation portion,
wherein the switch portion is provided on a lower surface of the frame;
a grip portion that grips the one end portion of the slide accommodated in the slide accommodation portion switched to the second state; and
a conveyor portion that conveys the slide gripped by the grip portion by moving the grip portion.

9. The slide conveyor apparatus according to claim 8, wherein a mount position of the one or more slides in the second state is tilted a predetermined angle with respect to a mount position of the one or more slides in the first state.

10. The slide conveyor apparatus according to claim 9, wherein the slide accommodation portion includes
a first accommodation portion that accommodates the one end portion of the one or more slides, and
a second accommodation portion that accommodates a part of the one or more slides excluding the one end portion, the second accommodation portion being spatially apart from the first accommodation portion, and
wherein the switch portion makes a switch from the first state to the second state by tilting the second accommodation portion.

11. The slide conveyor apparatus according to claim 10, wherein the switch portion makes a switch from the first state to the second state by tilting the second accommodation portion using one end portion of the second accommodation portion distant from the first accommodation portion as a fulcrum.

12. The slide conveyor apparatus according to claim 11, wherein the switch portion tilts the second accommodation portion using the one end portion of the second accommodation portion as a fulcrum by lifting the second accommodation portion from below.

* * * * *